(12) United States Patent
Klussmann et al.

(10) Patent No.: US 7,863,432 B2
(45) Date of Patent: Jan. 4, 2011

(54) NUCLEIC ACID MOLECULES ENCODING AKAP18 DELTA, A SPLICE VARIANT OF A PROTEIN KINASE A ANCHOR PROTEIN

(75) Inventors: Enno Klussmann, Berlin (DE); Alexander Oksche, Berlin (DE); Walter Rosenthal, Kleinmachnow (DE)

(73) Assignee: Forschungsverbund Berlin e.V., Berlin (DE)

( * ) Notice: Subject to any disclaimer, the term of this patent is extended or adjusted under 35 U.S.C. 154(b) by 277 days.

(21) Appl. No.: 10/526,768

(22) PCT Filed: Sep. 5, 2003

(86) PCT No.: PCT/EP03/09892

§ 371 (c)(1),
(2), (4) Date: Nov. 7, 2005

(87) PCT Pub. No.: WO2004/022591

PCT Pub. Date: Mar. 18, 2004

(65) Prior Publication Data

US 2006/0154330 A1    Jul. 13, 2006

(30) Foreign Application Priority Data

Sep. 6, 2002 (DE) .............................. 102 44 072
Feb. 7, 2003 (DE) .............................. 103 06 085

(51) Int. Cl.
C07H 21/04 (2006.01)
C12N 15/63 (2006.01)
C12N 1/20 (2006.01)

(52) U.S. Cl. ................. 536/23.5; 435/320.1; 435/252.3
(58) Field of Classification Search ................... None
See application file for complete search history.

(56) References Cited

FOREIGN PATENT DOCUMENTS

WO    WO 99/62933 A1    12/1999
WO    WO 02/38592 A2    5/2002

OTHER PUBLICATIONS

Trotter et al, Alternative splicing regulates the subcellular localization of A-kinase anchoring protein 18 isoforms. J Cell Biol. Dec. 27, 1999;147(7):1481-92.*
UniProt_8.4 database Accession No. AKA7G_HUMAN from Trotter et al, Alternative splicing regulates the subcellular localization of A-kinase anchoring protein 18 isoforms. J Cell Biol. Dec. 27, 1999;147(7):1481-92. Alignment with SEQ ID No. 1.*
Whisstock et al, Prediction of protein function from protein sequence and structure. Q Rev Biophys. Aug. 2003;36(3):307-40. Review.*
Galye et al, Identification of regions in interleukin-1 alpha important for activity. J Biol Chem. Oct. 15, 1993;268(29):22105-11.*
Klussmann, et al.: "Role and Identification of Protein Kinase A Anchoring Proteins in Vasopressin Mediated Aquaporin-2 Translocation" Kidney International, vol. 60, 2001, pp. 446-449.
Trotter et al.: "Alternative Splicing Regulates the Subcellular Localization of A -Kinase Anchoring Protein 18 Isoforms" The Journal of Cell Biology, vol. 147, No. 7, Dec. 27, 1999.
Klussmann et al.: "Protein Klinase A Anchoring Proteins Are Required for Vasopression-Mediated Translocation of Aquaproin-2 into Cell Membranes of Renal Principal Cells" The Journal of Biological Chemistry, vol. 274, No. 18, Feb. 19, 1999.
Oliveria et al.: "Imaging Kinase-AKAP79-Phosphatase Scaffold Complexes at the Plasma Membrane in Living Cells Using Fret Microscopy" The Journal of Cell Biology, vol. 160, No. 1, Jan. 1, 2003, pp. 101-112.
Klussman et al. "An inhibitory role of Rho in vasopressin-mediated translocation of aquaporin-2 into cell membranes of renal principal cells." Abstract Only.
Schneider et al. "Peptide design by artificial neural networks and computer-based evolutionary search." *Proc. Natl. Acad. Sci. USA* vol. 95, pp. 12179-12184, Oct. 1998.
Hundsrucker et al. "High-affinity AKAP7d—protein kinase A interaction yields novel protein kinase A-anchoring disruptor peptides." *Biochem. J.*, 396, 297-306, 2006.
Mary Louise Ruehr et al., "Cyclic AMP-dependent Protein Kinase Binding to A-kinase Anchoring . . . Protein Fusion Proteins," The Journal of Biological Chemistry, Nov. 12, 1999, vol. 274, No. 46, pp. 33092-33096.
Srinivasan Vijayaraghavan et al., "Protein Kinase A-anchoring Inhibitor Peptides Arrest Mammalian Sperm Motility", The Journal of Biological Chemistry, Feb. 21, 1997, vol. 272, No. 8, pp. 4747-4752.

* cited by examiner

*Primary Examiner* — Sheridan Swope
(74) *Attorney, Agent, or Firm* — Millen, White, Zelano & Branigan, P.C.

(57) ABSTRACT

The invention relates to polynucleotides which encode a protein kinase A anchor proteins (AKAP) and the use of such polynucleotides to generate AKAP polypeptides or fusion proteins containing AKAP proteins. The present invention also relates to methods of determining the interaction of AKAP proteins with regulatory subunits of protein kinase A and methods for identifying cell-permeable substances.

8 Claims, 15 Drawing Sheets

Fig. 1A

AKAP18δ

Amino acid sequence

MERPAAGEIDANKCDHLSRGEEGTGDLETSPV
GSLADLPFAAVDIQDDCGLPDVPQGNVPQGNPKRSKENRGDRNDHVKKRK
KAKKDYQPNYFLSIPITNKKITAGIKVLQNSILRQDNRLTKAMVGDGSFH
ITLLVMQLLNEDEVNIGTDALLELKPFVEEILEGKHLTLPFHGIGTFQGQ
VGFVKLADGDHVSALLEIAETAKRTFQEKGILAGESRTFKPHLTFMKLSK
APMLWKKGVRKIEPGLYEQFIDHRFGEEILYQIDLCSMLKKKQSNGYYHC
ESSIVIGEKDRKEPEDAELVRLSKRLVENAVLKAVQQYLEETQNKKQPGE
GNSVKAEEGDRNGDGSDNNRK

Nucleotide sequence (SEQ No. 1)

ATGGAGCGCCCCGCCGCGGGAGAAATAGATGCCAATAAGTGTGA
TCATTTATCAAGAGGAGAGGAAGGGACGGGGGACCTGGAGACCAGCCCTG
TAGGTTCTCTGGCAGACCTGCCGTTTGCTGCCGTAGACATTCAAGATGAC
TGTGGACTCCCTGATGTACCTCAAGGAAATGTACCTCAAGGAAACCCAAA
GAGAAGCAAAGAAAATAGAGGCGACAGGAATGATCACGTGAAGAAGAGGA
AGAAGGCCAAGAAAGATTATCAACCCAACTATTTCCTGTCCATTCCAATC
ACCAACAAAAAGATTACAGCTGGAATTAAAGTCTTGCAAAATTCGATACT
GAGACAGGATAATCGATTGACCAAAGCCATGGTCGGCGACGGCTCCTTTC
ACATCACCTTGCTAGTGATGCAGCTATTAAACGAAGATGAAGTAAACATA
GGTACCGACGCGCTTTTGGAACTGAAGCCGTTCGTTGAGGAGATCCTTGA
GGGGAAGCATCTGACTTTGCCCTTCCACGGGATTGGCACTTTCCAAGGTC
AGGTTGGCTTTGTGAAGCTGGCAGACGGAGATCACGTCAGTGCCCTCCTG
GAGATAGCAGAGACTGCAAAAAGGACATTTCAGGAAAAAGGCATCCTGGC
TGGAGAAAGCAGAACTTTTAAGCCTCACCTGACCTTTATGAAGCTGTCCA
AAGCACCAATGCTCTGGAAGAAGGGAGTGAGAAAAATAGAGCCTGGATTG
TATGAGCAATTTATCGACCACAGATTTGGAGAAGAAATACTGTACCAAAT
AGATCTCTGCTCCATGCTGAAGAAAAACAGAGCAATGGTTATTACCACT
GCGAGTCTTCGATCGTGATCGGTGAGAAGGACCGAAAGGAGCCTGAGGAT
GCTGAACTGGTCAGGCTCAGTAAGAGGCTGGTGGAGAACGCCGTGCTCAA
GGCTGTCCAGCAGTACCTAGAAGAGACACAGAACAAAAAGCAGCCGGGGG
AGGGGAACTCCGTCAAAGCTGAGGAGGGAGATCGGAATGGCGATGGCAGT
GATAACAACCGGAAGTGA

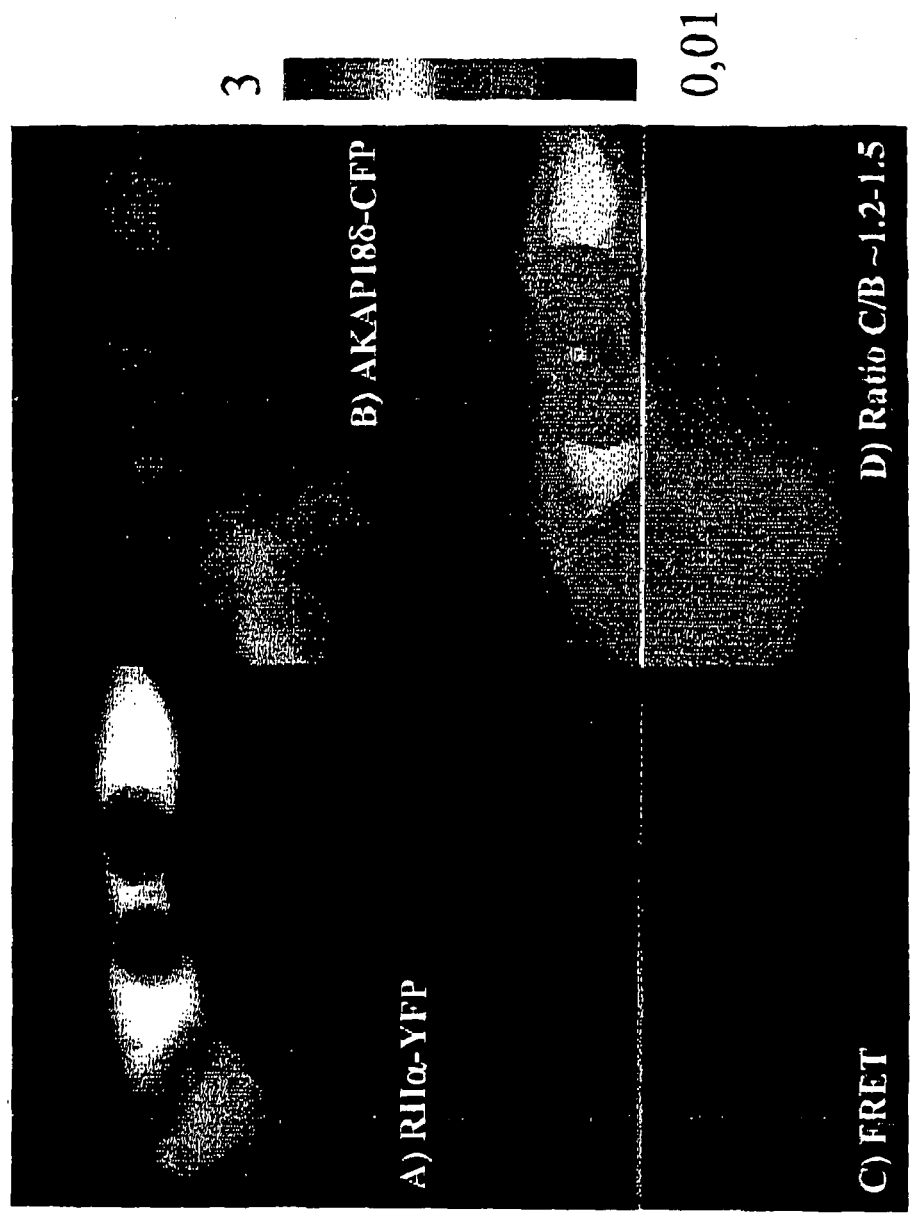
Fig. 2: Interaction of AKAP18δ-CFP and RIIα-YFP

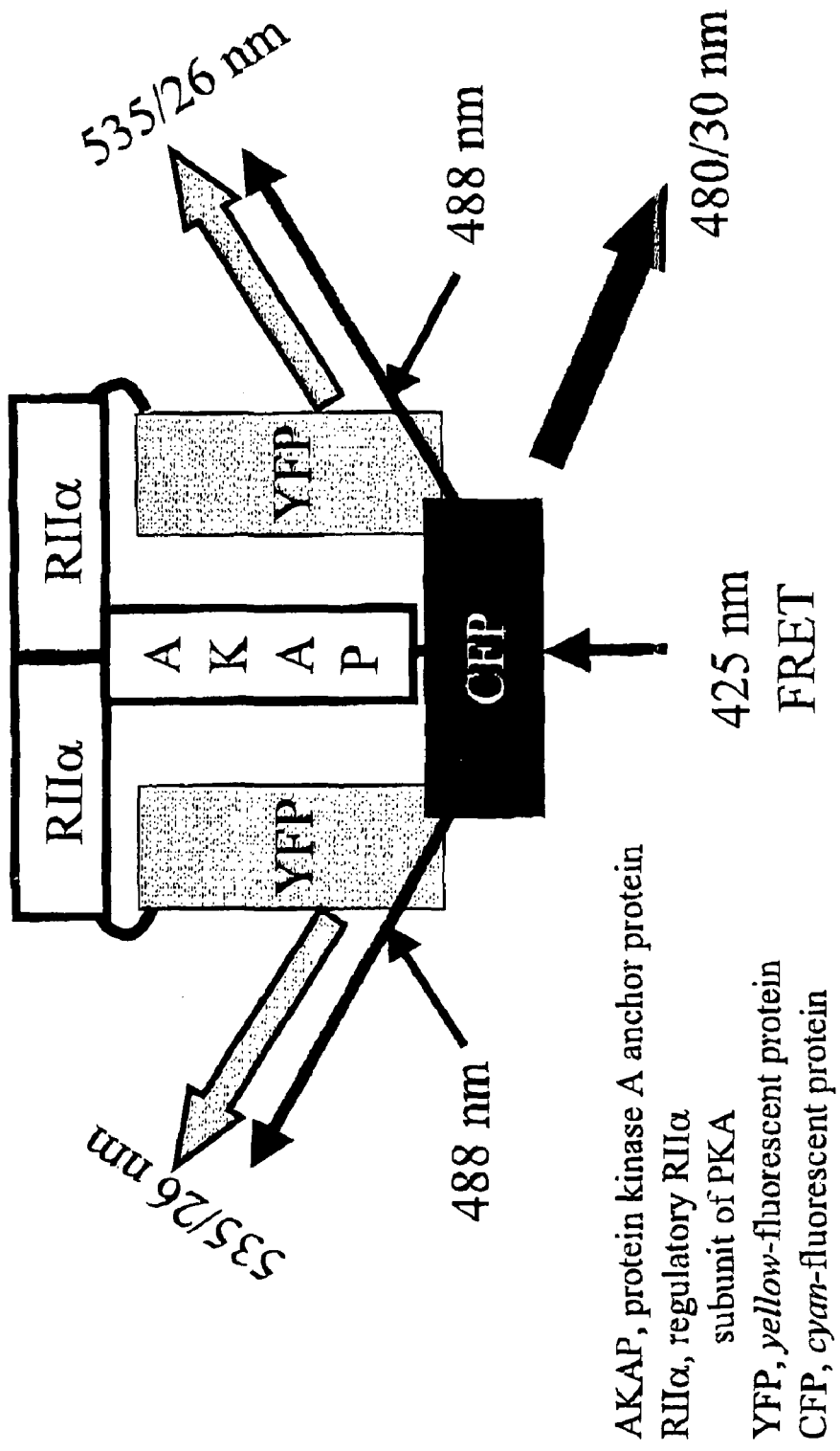
Fig. 3: *Fluorescent Resonance Energy Transfer* (FRET) between AKAP18δ-CFP and RIIα-YFP
AKAP, protein kinase A anchor protein
RIIα, regulatory RIIα subunit of PKA
YFP, *yellow*-fluorescent protein
CFP, *cyan*-fluorescent protein Bleaching of acceptor YFP (RIIα-YFP) results in an increase of fluorescence emitted by donor CFP (AKAP18δ-CFP)

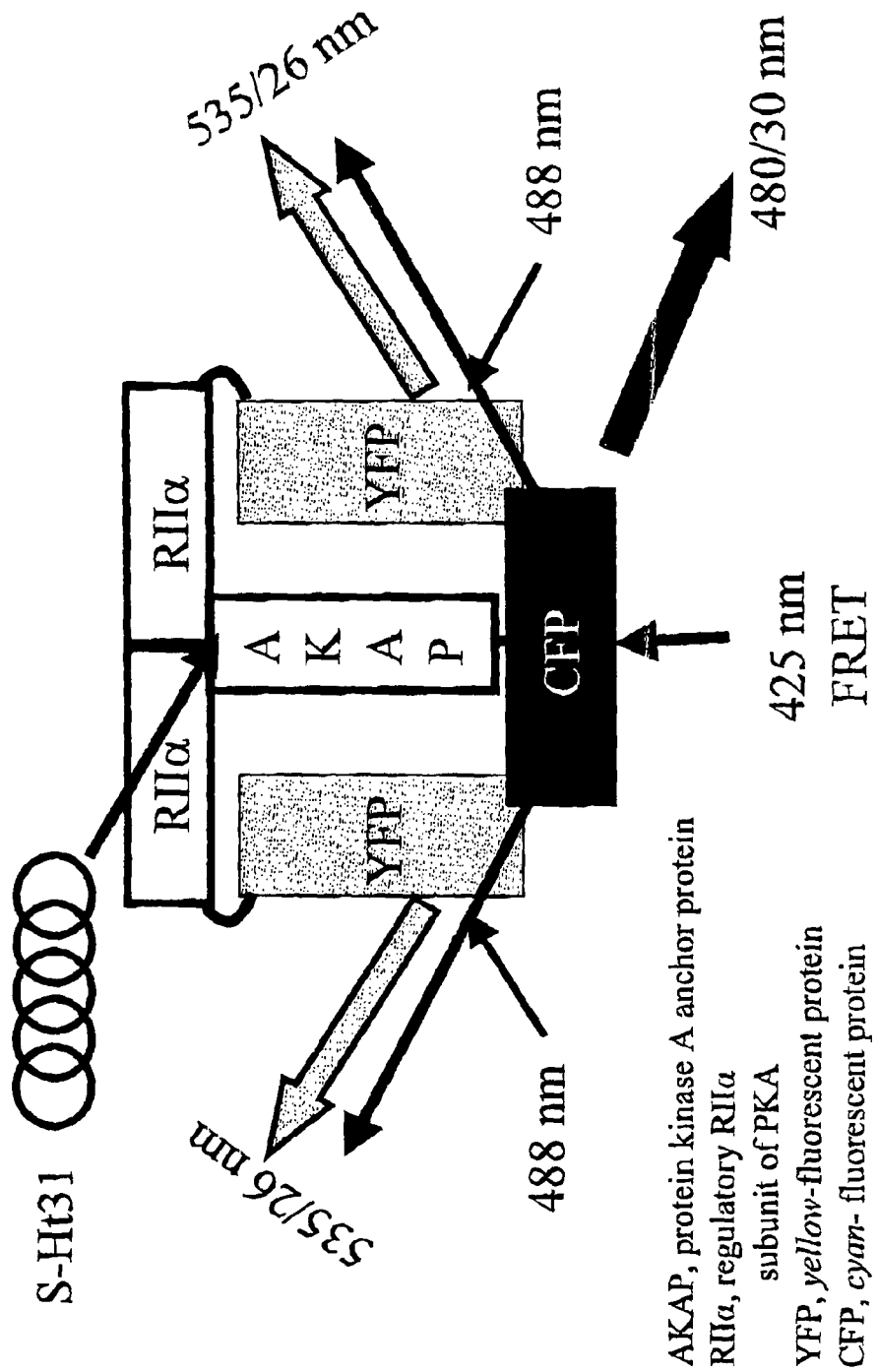
Fig. 5A: Inhibition of interaction of AKAP18δ-CFP and RIIα-YFP by peptide S-Ht31
AKAP, protein kinase A anchor protein
RIIα, regulatory RIIα subunit of PKA
YFP, *yellow*-fluorescent protein
CFP, *cyan*- fluorescent protein

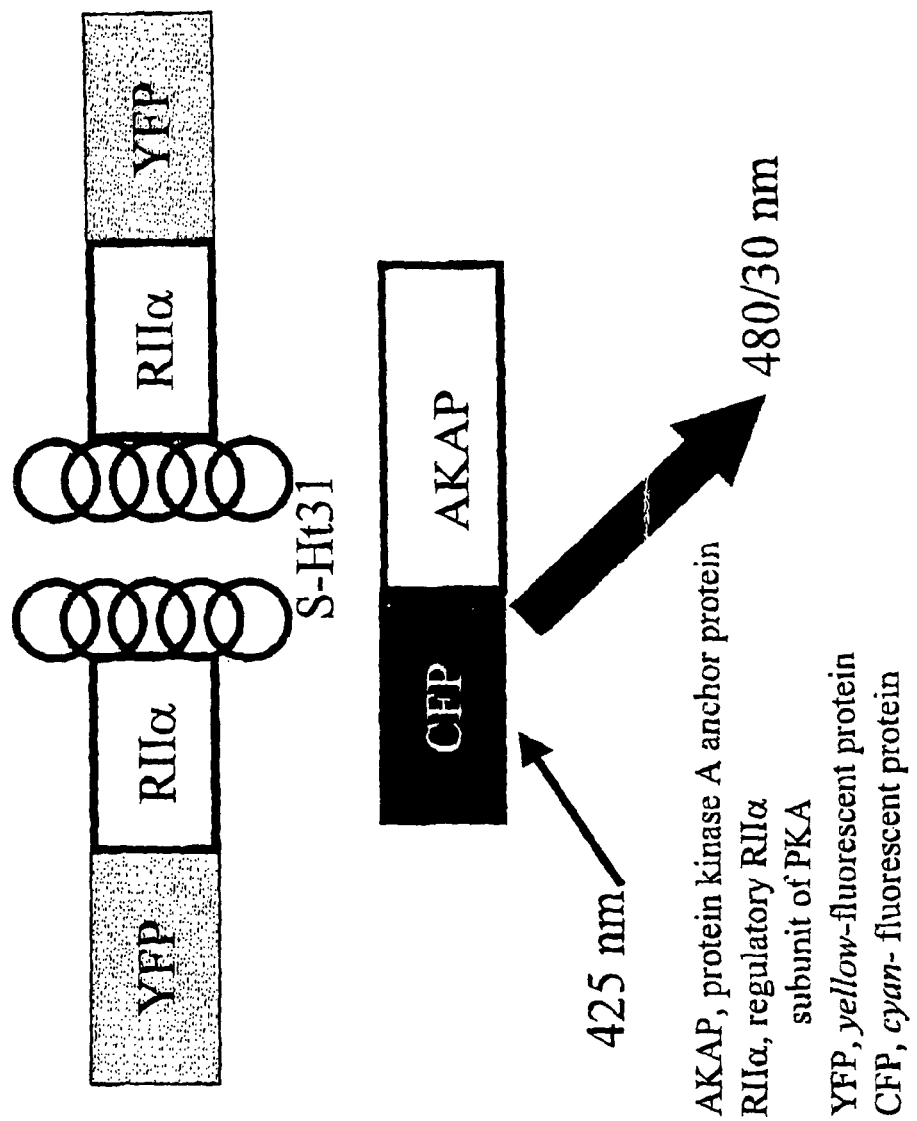
Fig. 5B: Result of inhibition of interaction between AKAP18δ-CFP and RIIα-YFP by S-Ht31
AKAP, protein kinase A anchor protein
RIIα, regulatory RIIα subunit of PKA
YFP, *yellow*-fluorescent protein
CFP, *cyan*- fluorescent protein

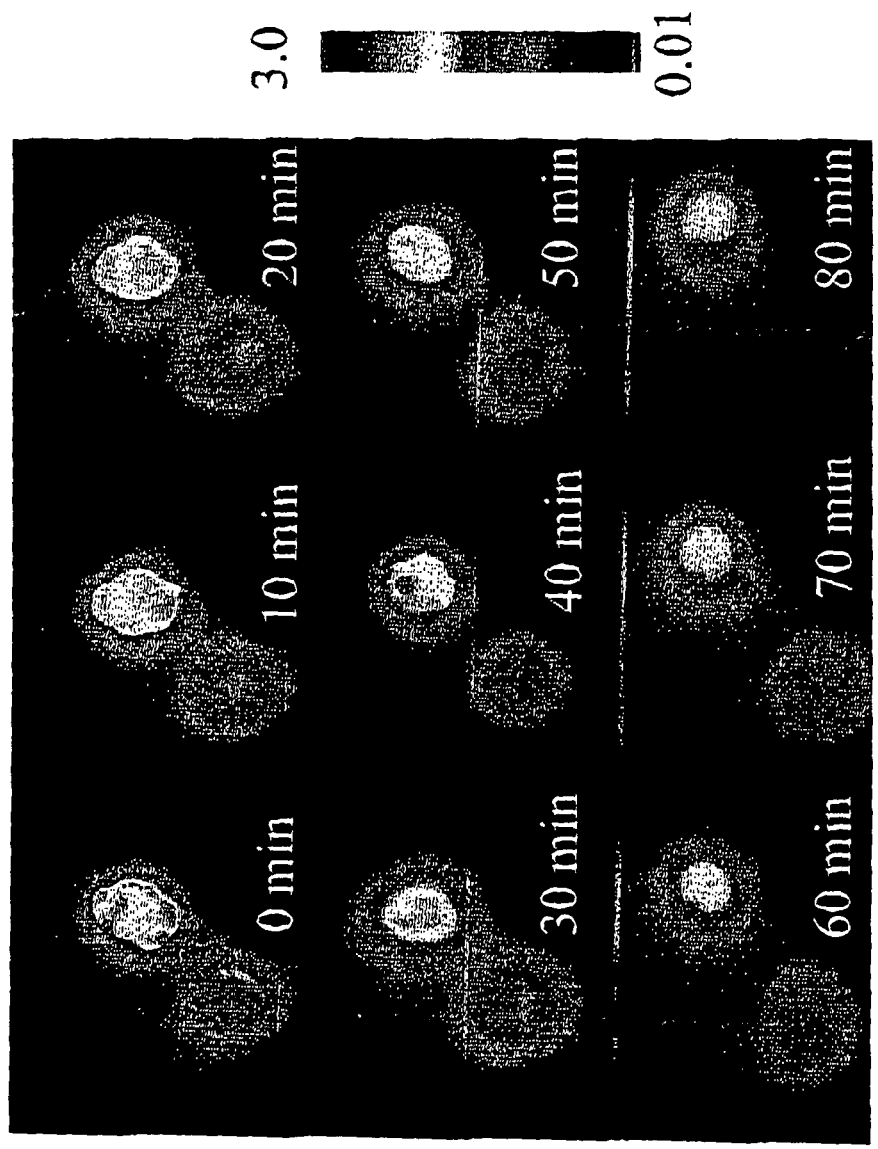
Fig. 6A: Inhibition of interaction of AKAP18δ-CFP and RIIα-YFP by peptide S-Ht31 – decrease of FRET signal

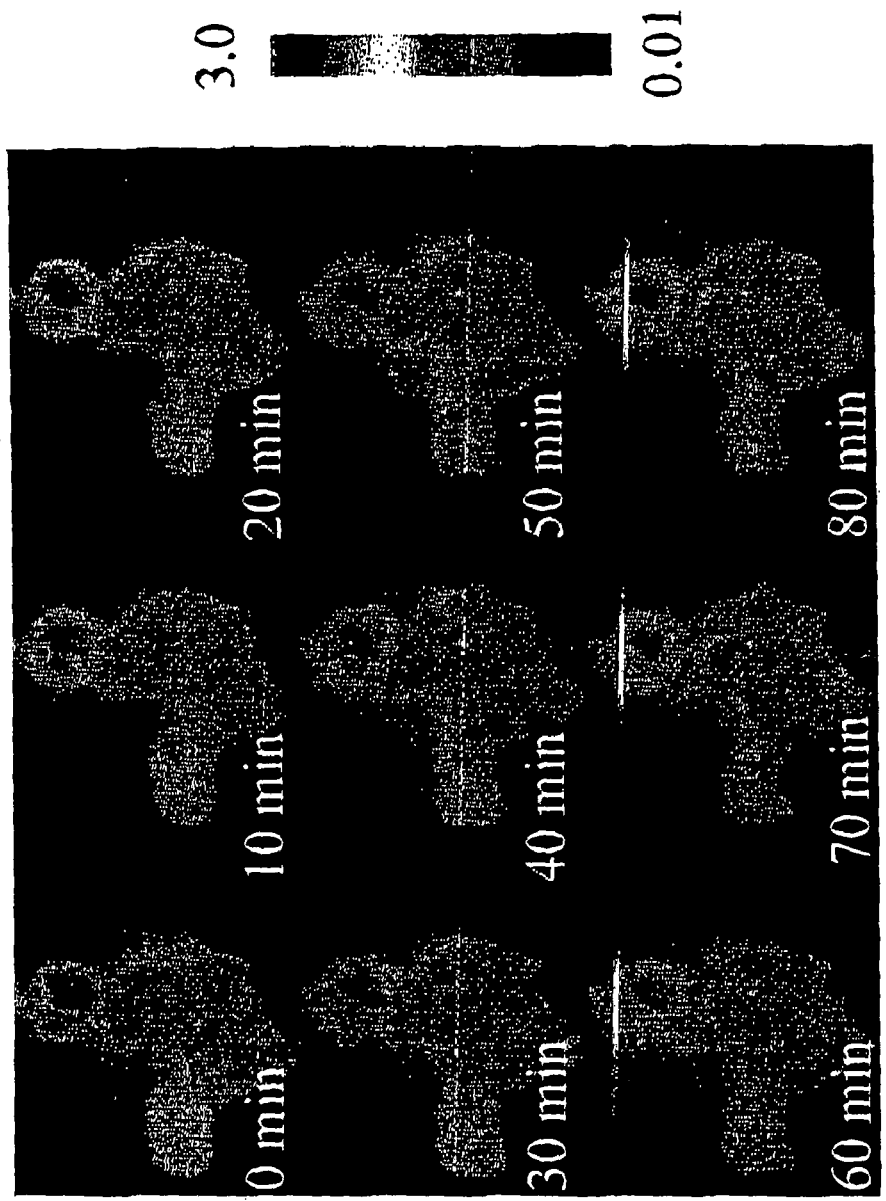
Fig. 6B: Peptide S-Ht31-P fails to inhibit interaction of AKAP18δ-CFP and RIIα-YFP - no decrease of FRET signal

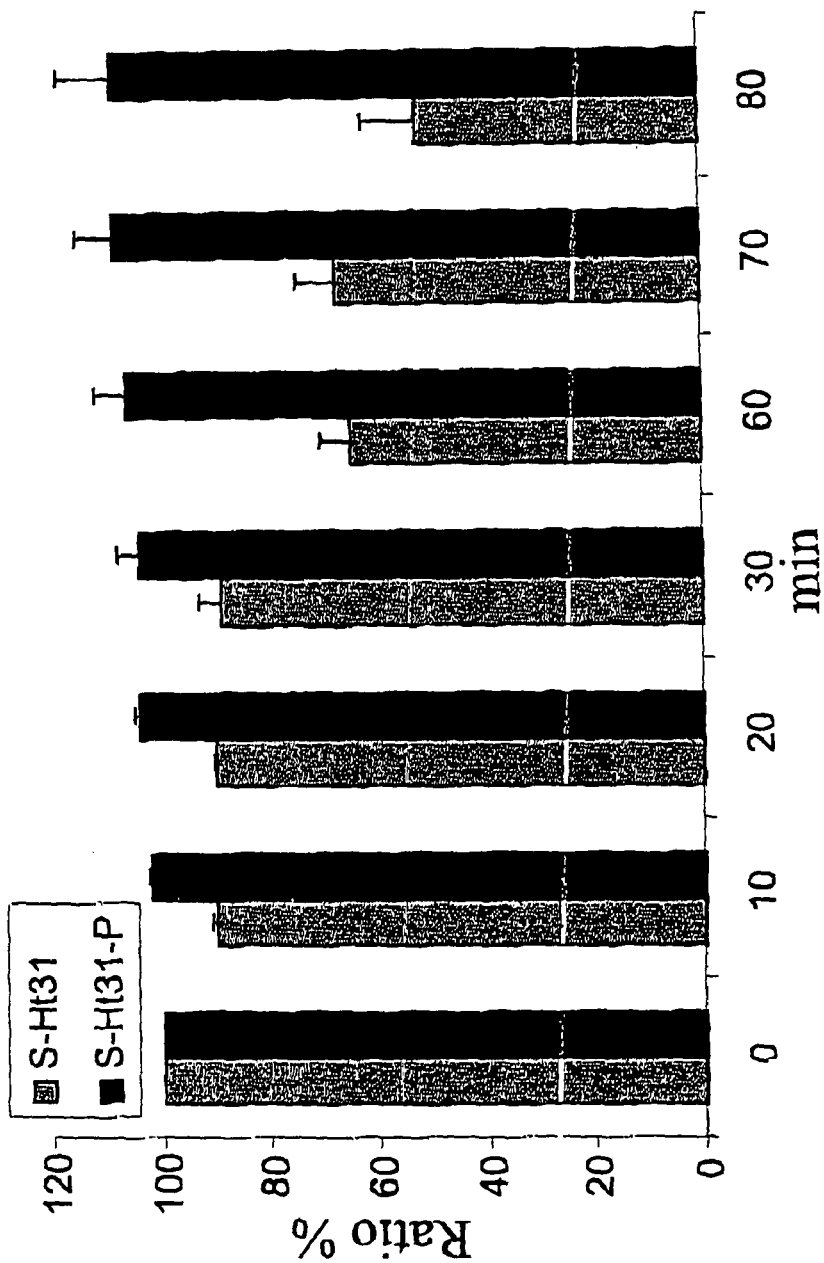
Fig. 6C: Changes in FRET signals (ratio 535/480) of AKAP18δ-CFP and RIIα-YFP in HEK293 cells in the presence of peptides S-Ht31 and S-Ht31-P Fig. 8A
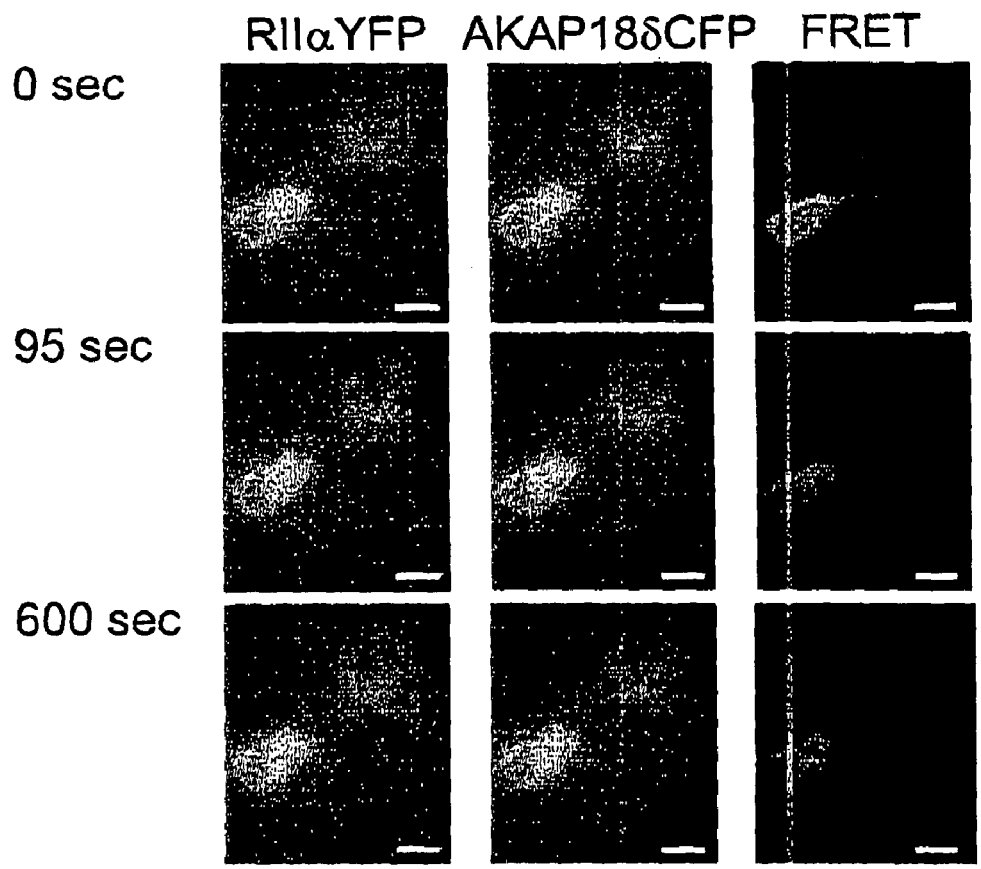
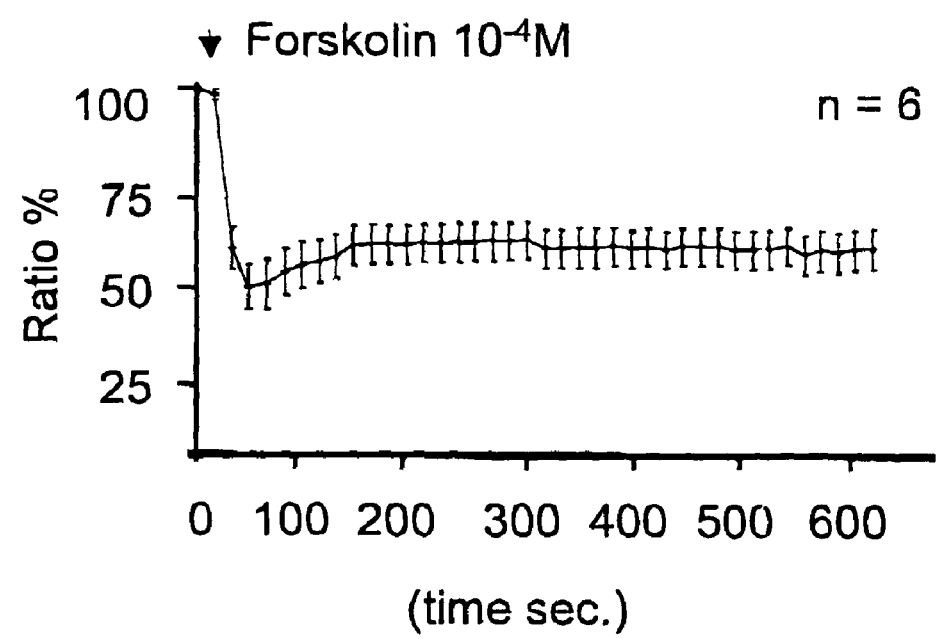

NUCLEIC ACID MOLECULES ENCODING AKAP18 DELTA, A SPLICE VARIANT OF A PROTEIN KINASE A ANCHOR PROTEIN

The invention relates to a nucleic acid sequence encoding a protein kinase A anchor protein, to the use of said nucleic acid sequence in a fusion protein, to a method of determining the interaction of said protein kinase A anchor protein with regulatory subunits of said protein kinase A, and to a method of identifying cell-permeable substances.

The biological activity of hormones and neurotransmitters is mediated via activation of signal cascades altering the phosphorylation state of effector proteins. Two classes of enzymes are involved in this reversible process: protein kinases and phosphoprotein phosphatases. Phosphorylation is effected by kinases catalyzing the transfer of the terminal phosphate group of ATP on specific serine or threonine residues, and dephosphorylation is mediated by phosphoprotein phosphatases. One mechanism of controlling and regulating such enzyme activities is compartmentation of these enzymes by association with anchor proteins located near their substrates. Protein kinase A (PKA) is one of these multifunctional kinases with broad substrate specificity which is anchored on subcellular structures by so-called protein kinase A anchoring proteins (AKAPs).

In many essential cellular processes such as contraction, secretion, metabolism, gene transcription, cell growth and division, the transduction of extracellular signals proceeds via G protein-coupled receptors, G protein Gs, activation of an adenyl cyclase, and formation of the second messenger cyclic adenosine monophosphate (cAMP). The effects of cAMP are mediated by the cAMP-dependent PKA.

In humans, the subunits of PKA are encoded by seven distinct genes located on different chromosomes. Three genes encode the isoforms of the catalytic subunits Cα, Cβ and Cγ, and four genes encode the isoforms of the regulatory subunits RIα, RIβ, RIIα and RIIβ.

The regulatory subunits show varying expression patterns. While RIα and RIIα are ubiquitous in tissues, the regulatory subunit RIβ is predominantly found in the brain.

The association of the RII subunits with intracellular compartments is mediated by AKAPs. The anchor proteins are a group of functionally related molecules characterized by the interaction with type I or type II of the regulatory subunits (RI and RII, respectively) of the PKA holoenzyme. The first anchor proteins have been isolated during affinity-chromatographic purification of the R subunits on cAMP-Sepharose. These associated proteins showed RII binding even after transfer onto a nitrocellulose membrane. This observation also forms the basis of the current method (RII overlay) of detecting AKAPs. It is a modified Western blot wherein radioactively labelled RII subunits rather than a primary antibody are used as probe.

Little is known about the functional significance of the RI-AKAP interaction. Although RIα is mainly found in the cytosol, a number of studies show anchoring in vivo. Dynamic anchoring of the RIα subunits—as opposed to static anchoring of RII subunits—seems to be of crucial significance to the cell. Thus, association of the RI subunits with the plasma membrane of erythrocytes and activated T lymphocytes has been described. In cAMP-mediated inhibition of T cell proliferation by type I PKA, localization of the enzyme possibly could be mediated by AKAPs. In knockout mice, which do not express any regulatory type II subunits in their skeletal muscle tissue, the RIα subunits bind to a calcium channel-associated AKAP, thereby obtaining normal, cAMP-dependent channel conductivity as a result of the proper availability of the catalytic subunits of PKA.

Furthermore, it has been shown in vivo that the catalytic subunits in the cell preferentially associate with the RII subunits, and that type I PKA holoenzyme is formed when the amount of free catalytic subunits exceeds the amount of free RII subunits.

Specificity in PKA anchoring is achieved by virtue of the targeting domain—a structural motif which, in contrast to the anchoring domain, is neither conserved in the sequence, nor in the structure of the AKAPs. Thus, AKAPs are anchored to structural elements in the cell by protein-protein interactions and to membranes by protein-lipid interactions.

The literature describes various AKAPs undergoing association with various cellular compartments, for instance with the centrosomes, mitochondria, the endoplasmic reticulum and Golgi apparatus, the plasma and nuclear membranes, and vesicles.

To date, the precise mechanisms of anchoring are known for only a few AKAPs. Thus, the myocardium-specific anchor protein mAKAP is anchored to the perinuclear membrane of the cardiomyocytes by a region including three spectrin-like repeat sequences. Two isoforms of AKAP15/18 are anchored to the plasma membrane via lipid modifications (myristoylation and palmitoylation). Three polybasic regions in the targeting domain of AKAP79 are involved in the localization of the protein on the inner postsynaptic membrane (PSD, postsynaptic density).

AKAPs were first characterized via the interaction with PKA. However, some of these proteins may also bind other enzymes involved in signal transduction. As a result of simultaneous anchoring of enzymes catalyzing opposing reactions, such as kinases and phosphatases, these AKAPs—also referred to as scaffolding proteins—can localize entire signal complexes in the vicinity of particular substrates, thereby contributing to the specificity and regulation of the cellular response to extracellular signals. AKAP79 was the first AKAP where interaction with a plurality of enzymes could be detected. Said protein binds protein kinase A, protein kinase C and the protein phosphatase calcineurin (PP2B), each enzyme being inhibited in bound condition. Distinct signals are required for the activation of each individual enzyme, which is why various second messengers such as cAMP, calcium and phospholipids may be present together at this position. Further examples are AKAP220, which localizes PKA and protein phosphatase PP1 on the peroxisomes, and the yotiao AKAP which, in addition to PKA, also binds protein phosphatase PP1. The CG-NAP AKAP not only binds PKA and protein phosphatase PP1, but also the rho-dependent kinase PKN (NGF (nerve growth factor)-activated protein kinase) and protein phosphatase PP2A.

In the prior art, an AKAP18γ is known, which is present in various tissues such as water channels or in the heart either in non-expressed form, or does not assume any function. Using well-known AKAPs, no success in visualizing the interaction, e.g. with PKA, has been made as yet. Merely by way of publications, e.g. Klussmann et al. (1999), it is known that an interaction must be assumed on the basis of certain results, which interaction itself could not be analyzed.

Other proteins may also undergo association with AKAPs. Thus, ezrin, a member of the cytoskeleton-associated ERM family ezrin, radixin and moesin, which has been identified as an AKAP, binds to a protein (EBP50/NHERF) which is involved in the regulation of the sodium-proton transport in the apical membrane of epithelial cells. AKAPs mediate the modulation of the conductivity of ion channels by localization of protein kinases and phosphatases in the vicinity of particular channel subunits probably regulated by phosphorylation and dephosphorylation.

The activity of the NMDA receptor is modulated by the yotiao AKAP which also binds protein phosphatase PP1. The phosphatase, which is active in bound condition, limits the channel conductivity of the NMDA receptor until the PKA is activated by cAMP, phosphorylating the ion channel or an associated protein so that the conductivity rapidly increases. It has also been shown that myristoylated Ht31 peptides inhibiting the interaction between PKA and AKAP suspend the cAMP-dependent inhibition of interleukin-2 transcription in Jurkat T cells, and that S-Ht31 peptides restrict sperm motility.

AKAPs are also involved in essential complex biological processes, such as insulin secretion in beta cells of the pancreas and in RINm5F cells (clonal beta cell line of rats) mediated by the hormone GLP-1 (glucagon-like peptide). The activation of PKA by GLP-1 results in phosphorylation of L-type calcium channels, favoring exocytosis of insulin from secretory granules. Ht31 peptide-mediated inhibition of PKA anchoring results in a significant reduction of insulin secretion. Said peptides neither affect cAMP formation nor the activity of the catalytic subunits of PKA. Furthermore, an increase in insulin secretion after application of GLP-1 could be detected following expression of wild-type AKAP18α in RINm5F cells compared to control cells failing to express AKAP18α.

To date, co-precipitation has been used to demonstrate that any new protein is an AKAP. To this end, an antibody against the candidate protein is produced to cause immunoprecipitation from cells or tissues wherein expression thereof is present. Thereafter, the presence of regulatory and/or catalytic PKA subunits in the precipitate is investigated using a Western blot. The presence of PKA subunits in the precipitate indicates that the candidate protein acts as an AKAP in vivo. Such proof can also be furnished vice versa by immunoprecipitation of the PKA subunits and subsequent detection of the AKAP in the precipitate.

However, the above experimental approach does not permit any conclusions as to the intracellular localization or in vivo situation of an AKAP-PKA complex. Furthermore, analysis of time and space resolution of interactions is not possible. In addition, specific AKAP inhibitors or activators cannot be identified with known methods at present.

The object of the invention is therefore to provide new nucleic acid sequences encoding structures which can be used in methods detecting the interaction between AKAP and PKA in vivo, thereby allowing conclusions as to the cellular localization of said interaction, which nucleic acid sequences can also be used in methods capable of detecting membrane-permeable substances, particularly peptides.

The present invention solves the above technical problem by providing an isolated nucleic acid sequence selected from the group comprising:
a) a nucleic acid molecule comprising a nucleotide sequence selected from the group consisting of SEQ ID No. 1 or complementary nucleotide sequences thereof,
b) a nucleic acid molecule which undergoes hybridization with a nucleotide sequence according to a) under stringent conditions,
c) a nucleic acid molecule comprising a nucleotide sequence having sufficient homology to be functionally analogous to a nucleotide sequence according to a) or b),
d) a nucleic acid molecule which, as a consequence of the genetic code, is degenerated into a nucleotide sequence according to a)-c), and
e) a nucleic acid molecule according to a nucleotide sequence of a)-d) which is modified and functionally analogous to a nucleotide sequence according to a)-d) as a result of deletions, additions, substitutions, translocations, inversions and/or insertions.

The conditions of hybridization are selected so as to exclude hybridization with well-known nucleic acid molecules, particularly those encoding well-known splicing variants.

Surprisingly, the nucleic acid sequences according to the invention can be used to detect the interaction of AKAP and PKA subunits in vivo, so that an AKAP-PKA complex can be assigned to a cellular compartment, the term AKAP in this context relating to the new splicing variant.

In the meaning of the invention, functional analogy to the above-mentioned nucleic acid sequences or to sequences hybridizing with said nucleic acid sequences implies that the encoded homologous structures during the interaction with PKA subunits exhibit features allowing conclusions as to the in vivo situation, cellular localization, and identification of specific AKAP inhibitors. More specifically, functionally analogous means that the encoded molecules show a behavior analogous to the new splicing variant AKAP18δ.

Using the new splicing variant, it is possible to solve problems that could not be solved by means of the well-known splicing variant AKAP18γ, for example. On a nucleic acid level, the differences between the well-known AKAP18γ and the AKAP18δ according to the invention are about 20%.

The protein kinase A anchor proteins AKAPγ and the AKAP18δ according to the invention are distinct splicing variants of the AKAP18 gene. Compared to AKAP18γ, AKAP18δ contains 27 additional amino acids at the N terminus, which amino acids are encoded by an exon. AKAP18δ is constituted of 353 and AKAP18γ of 226 amino acids. There is 75% identity between the two proteins in the overlapping sequence region.

These differences result in marked functional differences between the well-known and the new molecule. Thus, for example, AKAPδ—in contrast to AKAP18γ—is positioned on water channel-containing vesicles in a way so as to be capable of assuming essential functions. Furthermore, AKAPδ is located on $Ca^{2+}$ channels in the heart, assuming essential functions there, whereas AKAP18γ is not expressed in the heart at all. Accordingly, there are marked differences between the well-known splicing variant of AKAP18 and the new one according to the invention. The new splicing variant leads to new and surprising results. Thus, for example, particularly good and effective visualization of the interaction with PKA is possible when using AKAP18δ. Although there are structural similarities between the well-known AKAP18γ and the AKAP18δ according to the invention, the new molecules are better suited as a means for the inventive solution compared to the known ones. Neither on the basis of general knowledge in the art, nor as a result of a particular disclosure, a person skilled in the art might have assumed that the existing structural differences between the two molecules would be so small that there would be no essential influence on properties significant to the solution of the above technical problem and therefore could be neglected. Rather, in addition to common features, there are apparent structural and functional differences between AKAP18δ and AKAP18γ which can be seen in the fact that AKAP18δ is expressed in particular regions of the body, e.g. in $Ca^{2+}$ channels of the heart, whereas the well-known compound is not expressed there.

In another advantageous embodiment of the invention, the nucleic acid molecule has at least 80%, preferably 90% homology to the nucleic acid molecule according to the invention.

In another preferred embodiment of the invention, the nucleic acid molecule is a genomic DNA and/or an RNA, and in a particularly preferred fashion the nucleic acid molecule is a cDNA.

The invention also relates to a vector comprising at least one nucleic acid molecule according to the invention. Further, the invention relates to a host cell comprising said vector. In a particularly preferred fashion, the invention also relates to a polypeptide encoded by a nucleic acid molecule according to the invention. Such a polypeptide is preferably a new splicing variant of said AKAP18 (AKAP18δ).

The invention also relates to said polypeptide or protein which is encoded by the nucleic acid molecule according to the invention.

The invention also relates to a recognition molecule directed against said nucleic acid molecule, said vector, said host cell, and/or said polypeptide. Recognition substances in the meaning of the invention are molecules capable of interacting with the above-mentioned structures such as nucleic acid molecules or sequences, vectors, host cells and/or polypeptides or fragments thereof, particularly interacting in such a way that detection of said structures is possible. In particular, said recognition substances can be specific nucleic acids binding to the above-mentioned nucleic acid molecules or polypeptides, such as antisense constructs, cDNA or mRNA molecules or fragments thereof, but also antibodies, fluorescent markers, labelled carbohydrates or lipids. Of course, it is also possible that the recognition substances are not proteins or nucleic acids or antibodies, but instead, antibodies directed against same. In this event, the recognition substances can be secondary antibodies, in particular.

In a special embodiment of the invention, the recognition molecule is an antibody, an antibody fragment and/or an antisense construct, especially an RNA interference molecule.

The antibodies in the meaning of the invention bind the polypeptides, especially AKAP18δ, in a specific manner. The antibodies may also be modified antibodies (e.g. oligomeric, reduced, oxidized and labelled antibodies). The term "antibody" used in the present specification includes intact molecules, as well as antibody fragments such as Fab, F(ab')$_2$ and Fv capable of binding the particular epitope determinants of the polypeptides. In these fragments, the antibody's ability of selectively binding its antigen or receptor is partially retained, the fragments being defined as follows:

(1) Fab: this fragment which includes a monovalent antigen-binding fragment of an antibody molecule can be produced by cleavage of a complete antibody using the enzyme papain, an intact light chain and part of a heavy chain being obtained;
(2) the Fab' fragment of an antibody molecule can be produced by treatment of a complete antibody with pepsin and subsequent reduction, resulting in an intact light chain and part of a heavy chain; two Fab' fragments per antibody molecule are obtained;
(3) F(ab')$_2$: fragment of the antibody which can be obtained by treatment of a complete antibody with the enzyme pepsin with no subsequent reduction; F(ab')$_2$ is a dimer of two Fab' fragments held together by two disulfide bonds;
(4) Fv: defined as a fragment modified by genetic engineering, which includes the variable region of the light chain and the variable region of the heavy chain and is expressed in the form of two chains; and
(5) single-chain antibodies ("SCA"), defined as a molecule modified by genetic engineering, which includes the variable region of the light chain and the variable region of the heavy chain, which regions are linked by means of a suitable polypeptide linker to form a genetically fused single-chain molecule.

The term "epitope" used in the present invention relates to any antigen determinant on the polypeptide, especially AKAP18δ. Epitope determinants normally consist of chemically active surface groups of molecules, such as amino acids or sugar side chains, and normally possess specific characteristics of the three-dimensional structure, as well as specific charge characteristics.

The invention also relates to a vaccine or pharmaceutical composition including said nucleic acid molecule, said vector, said host cell, said polypeptide and/or said recognition molecule, optionally together with a pharmaceutically acceptable carrier. The pharmaceutically acceptable carriers are per se known pharmaceutical adjuvants and/or additives. These additives and excipients, per se known to those skilled in the art, can also be liposomes or structures or solutions and/or buffer mixtures well-known in genetic engineering or other substances from the galenic sector.

Furthermore, the invention relates to a kit including said nucleic acid molecule, said vector, said host cell, said polypeptide, said recognition molecule and/or said pharmaceutical composition. For example, the kit can be used as a diagnostic kit or as a detection kit to detect in particular AKAP inhibitors or AKAP-PKA interaction.

The invention also relates to a method for the detection of an AKAP-PKA interaction, comprising the steps of:
a) providing a first vector, especially a plasmid, comprising a nucleic acid molecule of the invention which encodes (i) an AKAP, especially an AKAP18δ, and (ii) a first marker, particularly a fluorescent protein,
b) providing a second vector, especially a plasmid, comprising a second nucleic acid molecule which encodes (i) a regulatory subunit of a protein kinase, preferably RIIα, RIIβ, RIα or RIβ, and (ii) a second marker, especially a fluorescent protein,
c) incorporating the first and second vectors in a cell, thereby transfecting the cell, and
d) performing a fluorescence resonance energy transfer (FRET) measurement, thereby detecting the AKAP-PKA interaction.

Surprisingly, the method according to the invention permits visualization of the AKAP-PKA interaction, preferably AKAP18-PKA and more preferably AKAP18δ-PKA interaction, in a living cell and consequently, assignment of the AKAP-PKA complex to a cellular compartment.

In a first step of the method according to the invention, two vectors or plasmids are provided, the first plasmid, for example, comprising the nucleic acid molecule of the invention, which encodes AKAP18δ, and at least one additional nucleic acid molecule which encodes a marker, preferably a fluorescent protein. The second plasmid also comprises at least two nucleic acid molecules, a first nucleic acid molecule encoding the regulatory subunit of a protein kinase, preferably RIIα, and another nucleic acid molecule encoding a second marker, particularly a second fluorescent protein. More specifically, first and second fluorescent proteins can be selected in such a way that—provided sufficient spatial proximity—fluorescence resonance energy transfer (FRET) between them is possible. Accordingly, the first fluorescent protein can be a cyan-fluorescent protein (CFP) and the second fluorescent protein can be a yellow-fluorescent protein (YFP), for example. Obviously, those skilled in the art will be familiar with the fact that a variety of molecules can be used in order to enable measurable interaction between fluorescent markers, e.g. fluorescence resonance energy transfer, or to modify, e.g. inhibit, an existing fluorescence resonance energy transfer in such a way that interaction of at least two marker molecules, especially fluorescent markers, can be detected. To this end, first and second vectors, being plasmids in particular, must have at least one structure allowing measurable detection as a label. In the meaning of the invention, the term marker or label relates to all structures or methods which can be used to generate a detectable, preferably quantifiable signal and, in particular, involve binding or effective linking to a nucleic acid or protein or fragment thereof. More specifically, the markers or labels are capable of generating detectable signals via fluorescence. In the context with the teaching of this invention, the interaction or a modification of such interaction—e.g. as inhibition—is preferably detected in the form of a FRET measurement. Of course, it is also possible to generate signals by means of radioactivity, colorimetry, gravimetric analysis, X-ray diffraction or absorption, magnetism, or enzymatic activity, which signals are measured separately, or to generate, inhibit or modify signals associated with a fluorescence or a fluorescence resonance energy transfer process, so that interaction of at least two biological components, preferably two proteins, more preferably between a protein kinase, preferably PKA, and a protein kinase A anchor protein, preferably AKAP18δ, can be detected. A probe in the meaning of the invention is e.g. a nucleic acid or an amino acid sequence having at least one label on one end or both ends or internally, said label preferably being a dye or marker capable of producing fluorescence, or a fluorescence-quenching dye or marker. Therefore, a probe in the meaning of the invention can also be a nucleic acid or amino acid sequence having at least one label capable of modifying, particularly inhibiting, a detectable signal. For example, such a probe can be a quencher structure affecting the fluorescence of e.g. a marker or dye, e.g. of a reporter dye, in association with an interaction between two molecules in such a way that measurable signal modification can be produced. Thus, for example, such a quencher structure can be designed in such a way that no fluorescence signal or no energy transfer signal can be detected as a result of interaction with a fluorescent dye when the structure capable of producing fluorescence and the structure capable of quenching are in close spatial proximity as required to this end, e.g. during interaction of proteinase A anchor proteins and protein kinases; in such a system a fluorescence signal or a non-modified fluorescence signal would be detectable for as long as interaction between the labelled structures exists. Accordingly, the terms quenching, fluorescence resonance energy transfer signal, or simply fluorescence, relate to structures and methods which, in case a fluorescent molecule and another fluorescent or quenching molecule are in close spatial proximity and one of these molecules is excited, cause transfer of a substantial part of the energy of the excited state to the quencher without radiation, or emission into the system with measurable radiation. For example, the energy transferred to the quencher can be lost without radiation, or can be emitted at an emission wavelength different from that of the fluorescent molecule. That is, the interaction between two proteins or nucleic acids encoding same, especially those associated with protein kinase A and protein kinase A anchor protein, can be detected either by emitted radiation or by radiationless transfer of the energy to a quencher.

A practical instruction for the selection of suitable fluorescence-quencher pairs for particular probes is available in the literature and exemplified in the following references: Pesce et al., ed., Fluorescence Spectroscopy (Marcel Dekker, New York, 1971), White et al., Fluorescence Analysis: A Practical Approach (Marcel Dekker, New York, 1970). The literature also includes references providing detailed tables of fluorescent and chromogenic molecules and their relevant optical properties for the selection of fluorescence-quencher pairs; see e.g. Berlman, Handbook of Fluorescence Spectra of Aromatic Molecules, $2^{nd}$ edition (Academic Press, New York, 1971), Griffiths, Colour and Constitution of Organic Molecules (Academic Press, New York, 1976), Bishop, ed., Indicators (Pergamon Press, Oxford, 1972), Haugland, Handbook of Fluorescent Probes and Research Chemicals (Molecular Probes, Eugene, 1992). Furthermore, the literature includes a detailed instruction for the derivatization of fluorescent and quencher molecules for covalent binding via common reactive groups which can be attached to an oligonucleotide; cf., U.S. Pat. No. 3,996,345, U.S. Pat. No. 4,351,760.

Exemplary fluorescence-quencher pairs can be selected from xanthene dyes, including fluoresceins and rhodamine dyes. Many suitable forms of these compounds are commercially available and include substituents on their phenyl groups which can be used as binding site or as a binding functionality for binding to an oligonucleotide. Another group of fluorescent compounds are naphthylamines having an amino group in the α- or β-position. Naphthylamino compounds include 1-dimethylaminonaphthyl-5-sulfonate, 1-anilino-8-naphthalenesulfonate and 2-p-toluidinyl-6-naphthalenesulfonate. Other dyes include 3-phenyl-7-isocyanatocoumarin, acridines such as 9-isothiocyanatoacridine orange, N-(p-(2-benzoxazolyl)phenyl)maleimide, benzoxadiazoles, stilbenes, pyrenes. Furthermore, preferred fluorophores are SYBR Green, Hex, TET, VIC, JOE, NED, Redmond Red, Alexan Red, Cascade Blue, Yakima Yellow, Cy3, Cy3.5, Tamra/Cy3, Texas Red, ROX, Cy5, Cy5.5, carboxyrhodamines, LC705 and/or LC640. As quenchers, it is also possible to use Tamra, rhodamine, BHQ1 to BHQ3, Dansyl, Dabcyl, ElleQuencher and/or methyl orange, for example. A conjugate of nucleic acid samples with Minor Grove Binder (MGB) may also be preferred. For example, such structures have been described in Kutyavin et al., 2000, Nucleic Acids Research, and are incorporated in the present disclosure by way of reference.

According to the invention, two types of quenching processes or processes modifying fluorescence radiation can be distinguished, one being dynamic fluorescence quenching by collision processes and the other static fluorescence quenching by complex formation between the fluorophore, i.e., the marker or probe and the quencher molecules of the probe quencher. Accordingly, quenching results in a decrease of the quantum yield detectable by fluorescence excitation of the labelled probe. However, at very high concentrations, e.g. on a particular nucleic acid section, the probes may also tend to undergo so-called self-quenching, that is, individual molecules are perturbed in their motion in such a way that—as a result of the high probe density—a quenching effect likewise occurs.

In the meaning of the invention, e.g. a separately generated fluorescence signal, a fluorescence resonance energy transfer (FRET) signal, as well as a quenched signal, can also be used to detect an AKAP-PKA, a FRET signal being preferred. In particular, a FRET signal is obtained when using the fluorescent substances CFP and YFP.

The two plasmids that are provided are used to transfect a cell. Transfection in the meaning of the invention can be effected using chemical, physical and/or biological transfection methods. For example, chemical transfection can be effected using DEAE-dextran, dendrimers or calcium phosphate. In physical transfection it is possible, for example, to modify the membranes of cells via electroporation in such a way that the transfecting plasmid DNA is incorporated by the cells. Another method of physical transfection is e.g. microinjection or incorporation of DNA by bombardment with gold particles, for example. Methods of biological transfection are e.g. receptor-mediated transfection, receptor-mediated transfection supported by viral components, and lipofection. Those skilled in the art will be familiar with a variety of transfection techniques. Cells suitable for transfection can be prokaryotic or eukaryotic cells, e.g. bacterial, yeast, insect, plant or mammal cells, but also organisms such as transgenic animals or plants. Preferred in the eukaryotic systems are the mammal cell lines NSO, SP2/0, CHO-K1, CHO dhfr−, COS-1, COS-7, K562, Percy 6, or preferably HEK293 cells, preferably CD8 cells, LCCPK1, HeLa cells, MDCK2 cells, MCF7, fibroblasts, MCF7, NIH3T3.

Following co-transfection of the cells with the two plasmids under conditions well-known to those skilled in the art, the two fusion proteins—constituted of AKAP and the first fluorescent protein, and of the regulatory subunit of a protein kinase and the second fluorescent protein—are expressed. Provided the expressed fusion proteins do interact, such interaction can be detected, particularly in living organisms such as cells, on the basis of the interaction of the fluorescent proteins using the fluorescence resonance energy transfer technique. The fluorescence resonance energy transfer technique is based on an energy transfer from the first fluorescent protein to the second fluorescent protein, which transfer, however, is achieved only if the two fusion proteins are in close proximity to each other. The fusion proteins achieve such proximity particularly in those cases where the AKAP protein directly binds to the regulatory subunit of the protein kinase. In this event, fluorescence resonance energy transfer can be detected.

The system can also be used to identify substances inhibiting the interaction between AKAP and regulatory subunits, preferably RIIα, but also RIIβ, RIα and β of PKA.

Owing to the provision of the method according to the invention, a person skilled in the art is able to modify the procedure at will. More specifically, it is possible to examine whether particular molecules have an influence on the interaction of AKAP and PKA, in particular of AKAP18δ and RIIα. To this end, for instance, the method according to the invention can be performed in the presence and in the absence of the molecule to be investigated, and a comparison of performing the method with and without the molecule to be investigated will provide an indication as to the inhibitive character of the molecule. If, for example, no FRET signal is measured in the presence of said molecule, this would indicate that the molecule inhibits the interaction between AKAP and PKA.

Those skilled in the art will known which control tests could be used to exclude the possibility that the molecule itself suppresses the FRET; ways of detecting whether the molecule affects, preferably inhibits, AKAP, PKA subunits, or specific interactions thereof are also well-known in the art.

The identification of specific AKAP inhibitors bears a great therapeutic potential. AKAP-PKA interactions are of significance in various exocytotic processes, the misregulation gives rise to diseases such as diabetes insipidus, diabetes mellitus, hypertension, gastric ulceration or thyroidal diseases. Heart failures involve PKA-mediated hyperphosphorylation of an ion channel, i.e., the ryanodin receptor (calcium channel). Substances specifically inhibiting particular AKAPs could be used as pharmaceuticals in such diseases.

The method is also suitable for examining the membrane permeability of peptides. At present, there is no means of directly detecting or quantifying the membrane transfer of peptides. In particular, this can be achieved by producing a conjugate of the molecule to be investigated, especially a peptide, and S-Ht31 or a mixture with the peptide Ht31. However, any RII binding domain of any AKAP is possible.

In a special embodiment of the invention, the cell is contacted with a membrane-permeable peptide. For example, it is possible to perform one fluorescence resonance energy transfer measurement with no addition of membrane-permeable peptide and another one with addition of membrane-permeable peptide, thereby allowing detection as to whether the membrane-permeable peptide modifies, particularly prevents, AKAP-PKA interaction. For example, a continuous decrease of the fluorescence resonance energy transfer signal during measurement indicates inhibited interaction between AKAP and the regulatory subunit of the protein kinase in the presence of the membrane-permeable peptide. Furthermore, it is possible to use well-known membrane-permeable peptides inhibiting interaction between AKAP and PKA, the membrane-permeable peptides being examined for particular modifications, such as amino acid deletions or substitutions, in order to obtain an indication as to which amino acids in a membrane-permeable peptide are essential for suppression or promotion of the AKAP-PKA interaction.

The new aspect of the method according to the invention lies in the visualization of the AKAP-PKA interaction in a living cell and in the potential of assigning the AKAP-PKA complex to a cellular compartment.

However, this method spans a much wider range of uses. It allows for a high-throughput process for the identification and quantitative analysis of substances affecting the AKAP-PKA interaction. Moreover, it is possible to determine the membrane-permeating capability of peptides.

The invention also relates to the use of the inventive nucleic acid, said vector, said host cell, said polypeptide, said recognition molecule, said pharmaceutical composition, said kit and/or the inventive method in the detection of an AKAP-PKA interaction, an AKAP and/or PKA inhibition and/or a membrane-permeable peptide. As a result of providing the structures and methods according to the invention, a person skilled in the art can make use thereof in a number of fields of basic research and in the clinical sector. For example, it is possible to examine whether a molecule is an inhibitor of AKAP or PKA. Also, it is possible to examine whether a molecule modifies the interaction of AKAP and PKA. Furthermore, it is possible to detect whether a molecule, particularly a peptide, is membrane-permeable.

Without intending to be limiting, the invention will be explained in more detail with reference to the following examples.

BRIEF DESCRIPTION OF THE DRAWINGS

Various features and attendant advantages of the present invention will be more fully appreciated as the same becomes better understood when considered in conjunction with the accompanying drawings, in which like reference characters designate the same or similar parts throughout the several views, and wherein:

FIG. 1 shows the polypeptide (SEQ ID NO: 2) and polynucleotide (SEQ ID NO: 1) sequence of AKAP18δ.

FIG. 2 demonstrates co-expression of AKAP18δ-CFP and RIIα-YFP proteins in HEK293 cells. Expression of RIIα-YFP was detected by excitation at 488 nm and measurement of the emitted fluorescence at 535/26 nm (FIG. 2A), and that of AKAP18δ-CFP by excitation of fluorescence at 425 nm and measurement of the emitted fluorescence at 480/30 nm (FIG. 2B). FIG. 2C shows a similar distribution of the illustrated YFP emission as in FIG. 2A. Consequently, an energy transfer from CFP to YFP has occurred. FIG. 1D shows a color-coded illustration of the calculated 535/480 ratio of approximately 1.2-1.5 of FRET signals in HEK293 cells.

FIG. 3 is a schematic diagram of fluorescence resonance energy transfer (FRET) technology which is used in the determination of interaction of the expressed fusion proteins AKAP18δ-CFP and RIIα-YFP in a cell.

FIG. 4 shows the specificity of the measured FRET signals, as examined using acceptor bleaching protocol.

FIG. 5A is a schematic diagram showing the inhibition of interaction of AKAP18δ-CFP and RIIα-YFP by peptide S-Ht31. FIG. 5B is a schematic diagram showing the effect of such inhibitory peptides on FRET signals.

FIG. 6A shows the color-coded FRET signal (535/480 ratio) from AKAP18δ to RIIα in two HEK293 cells. FIG. 6B shows cells incubated with ineffective control peptide S-Ht31-P which has no influence on the AKAP-RII interaction. FIG. 6C shows the summarized data obtained from FIGS. 6A and B, illustrating the change of the FRET signal (in %) as a function of time. The graphic diagram shows the FRET signal change observed on the cells in the presence of S-Ht31 or S-Ht31-P.

FIG. 8 shows that AKAP18δ plays a role in the signal cascade resulting in translocation of AQP2 into the apical plasma membrane of renal chief cells. FIG. 8A: CD8 cells were cotransfected with plasmids encoding RIIα-YFP and AKAP18δ-CFP. The FRET was measured prior to and after stimulation of the cells with forskolin (100 μM). Illustrated are two representative cells, each one co-expressing two fusion proteins. The FRET was measured prior to forskolin administration (0 s) and 95 and 600 s later on (95 s and 600 s). The FRET signal (535/480 nm ratio) is coded in pseudo-colors. B: Quantitative analysis of the effect of forskolin on the FRET signal (n=6 cells). Scale 20 μm.

EXAMPLES

Figure 4A:
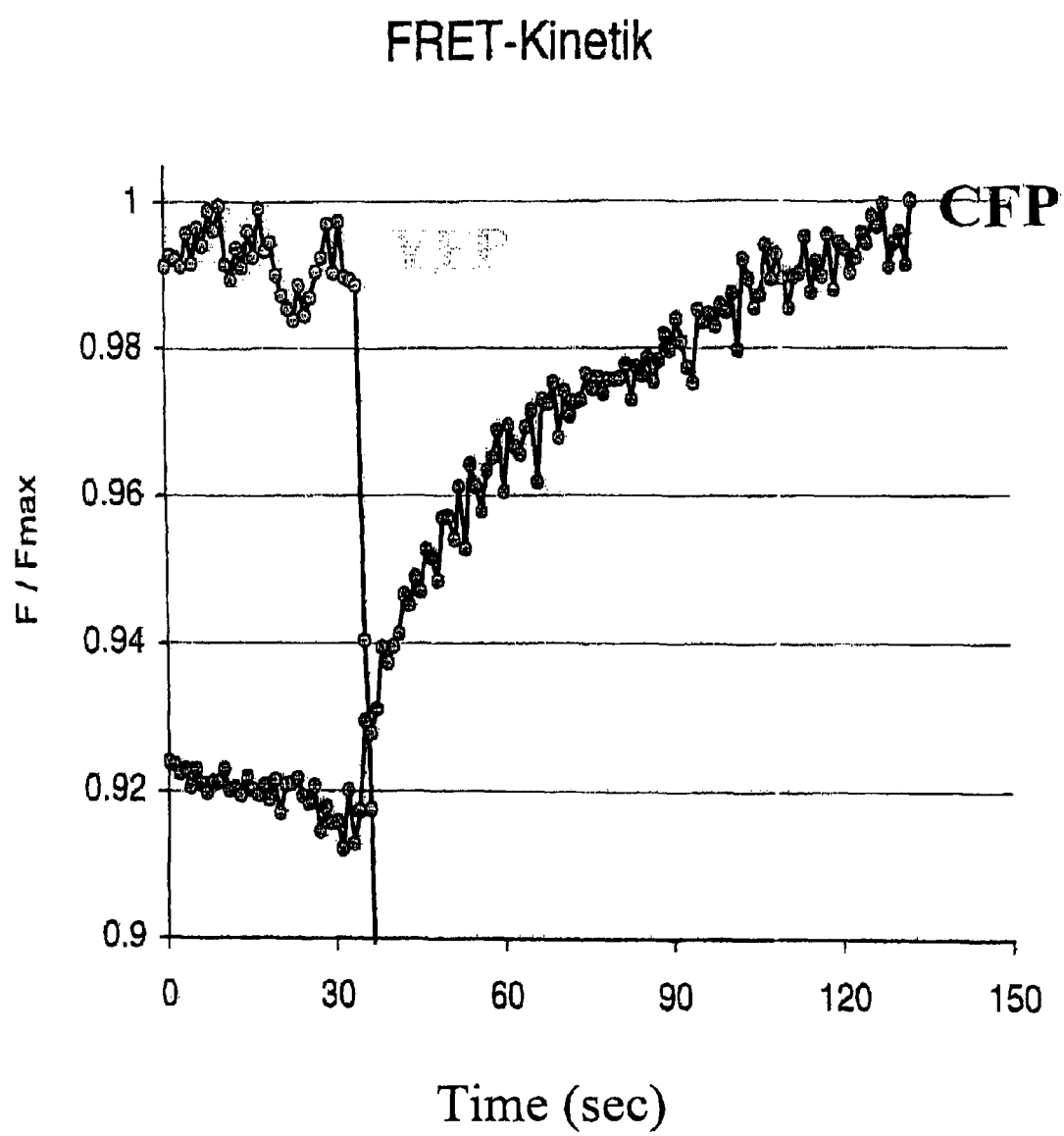
FIG. 4A describes the kinetics of the fluorescence emitted by YFP and CFP, illustrating the ratio $F/F_{max}$ as a function of time (time in s). $F_{max}$ corresponds to maximum emission of YFP and CFP, respectively.

First of all, the cDNA of a new splicing variant of the protein kinase A anchor protein (AKAP) AKAP18 was identified and isolated (FIG. 1; SEQ ID NO: 1), said variant being referred to as AKAP18δ. The AKAP18δ cDNA was cloned into the commercially available vector PECFP (BD Biosciences, Clontech Heidelberg). The cDNA of the regulatory subunit RIIα of human protein kinase A, supplied by Prof. Dr. K. Tasken (University of Oslo), was cloned into the commercially available vector pEYFP (BD Biosciences, Clontech, Heidelberg). Eukaryotic HEK293 cells (GBF, Brunswick) were co-transfected with the plasmids.

The interaction of the expressed fusion proteins AKAP18δ-CFP and RIIα-YFP was measured in the HEK293 cells using the fluorescence resonance energy transfer (FRET) technology (schematic diagram in FIG. 3). The FRET signals result from an energy transfer from CFP to YFP, which is only possible when the two proteins are in close proximity to each other (<10 nm). Such close proximity of CFP and YFP is achieved only when AKAP18δ directly binds the RIIα subunit. In this event, a FRET can be detected. The specificity of the interaction between AKAP18δ and RIIα can be verified by measuring the FRET in the presence of the membrane-permeable peptide S-Ht31 which prevents interaction between AKAP and the RII subunit. A continuous decrease of the FRET signal during measurement indicates inhibition of the interaction between AKAP18δ and RIIα.

The sequence of the S-Ht31 peptide corresponds to that of the PKA binding domain (RII binding domain) of AKAP Ht31. It forms an amphipathic helix, undergoing competitive binding to the regulatory PKA subunits. In this way, it prevents interaction with AKAP18δ. The peptide achieves membrane permeability by coupling to a stearate residue on the N terminus (Klussmann et al., J. Biol. Chem. 274, 4934-4938, 1999). Peptides with the same amino acid sequence (Ht31) which do not bear a stearate residue and therefore lack membrane permeability will not change the FRET signal in the system. Likewise, stearate-coupled S-Ht31 peptide obtained by insertion of two prolines perturbing the amphipathic helix does not change the FRET signal.

Part of the characterization of a newly identified AKAP is to demonstrate that it would act as AKAP in vivo, i.e., as a PKA counterpart in interaction. The method according to the invention permits detection of interaction between AKAP18δ and the RIIα subunits of PKA in living cells. Hence, the method is suited to demonstrate that AKAP18δ acts as AKAP in vivo. At the same time, the system allows conclusions as to the intracellular localization of the AKAP18δ-RIIα complex.

AKAPs represent a family of more than 50 proteins whose function cannot be manipulated by means of specifically interacting substances as yet. The S-Ht31 peptide which has been used to inhibit binding of AKAP18δ and RIIα (see above) is the only known substance at present which has an influence on the AKAP function. It inhibits the AKAP-PKA interaction, but decouples binding between any AKAP and all regulatory PKA subunits. In specific high-throughput investigations using FRET measurements, this developed system is intended to identify membrane-permeable peptides, as well as low-molecular weight non-peptide substances, which specifically inhibit the interaction between AKAP18δ and RIIα.

Production of Plasmids Encoding the Fusion Proteins AKAP18δ-CFP and RIIα-YFP

The coding region of the AKAP18δ cDNA identified by us (FIG. 1; SEQ ID NO: 1 sequence AKAP18δ) was amplified using polymerase chain reaction (PCR). To this end, forward primer (position in AKAP18δ: by 57-76) having the sequence 5' CTC GAG CTC AAG CTT CGA ATT CTG ATG GAG CGC CCC GCC GCG GG 3' (SEQ ID NO: 3) and reverse primer (position in AKAP18δ: by 1095-1118) having the sequence 5' GGC GAC CGG TGG ATC CCG GGC CCG GTT GTT ATC ACT GCC ATC GCC 3' (SEQ ID NO: 4), which bear an EcoRI and a BamHI restriction site, respectively, were employed. The Advantage cDNA Polymerase Mix was used as polymerase according to the manufacturer's instructions. The required 10.times. PCR buffer was supplied together the Advantage cDNA Polymerase Mix. The nucleotides DATP, dCTP, dGTP and dTTP were pipetted into the PCR batch as a dNTP mix (reaction batch see below).

The cDNA encoding the RIIα was amplified from the plasmid using PCR. To this end, forward primer (position in RIIα: by 190-210) having the sequence 5' TCA GAT CTC GAG CTC AAG CTT CGA ATT CTG ATG AGC CAC ATC CAG ATC CCG 3' (SEQ ID NO: 5) and reverse primer (position in RIIα: bp 1382-1401) having the sequence 5' GAC CGG TGG ATC CCG GGC CTG CCC GAG GTT GCC CAG AT 3' (SEQ ID NO: 6), which bear an XhoI and a BamHI restriction site, respectively, were employed. Again, the Advantage cDNA Polymerase Mix was used as polymerase. Likewise, the above-described 10×PCR buffer and the dNTP mix were employed.

The batches for the PCR reactions to amplify AKAP18δ and RIIα were as follows:

| | |
|---|---|
| DNA | 5 µl |
| dNTP mix [10 µM] | 1 µl |
| Forward primer [10 µM] | 1 µl |
| Reverse primer [10 µM] | 1 µl |
| Advantage cDNA Polymerase mix (5 units/µl) | 0.2 µl |
| H$_2$O | 41.8 µl |
| Total volume | 50 µl |

Reaction conditions:

| | |
|---|---|
| 1 cycle | 95° C., 5 min |
| 30 cycles | 94° C., 30 s |
| | 58° C., 30 s |
| | 72° C., 2 min |
| 1 cycle | 72° C. 10 min |
| 4° C., ∞ | |

The resulting AKAP18δ cDNA amplificate (length: 1061 bp) was treated with the restriction enzymes EcoRI and BamHI, and the resulting RIIα cDNA amplificate (length: 1211 bp) with the restriction enzymes XhoI and BamHI. Subsequently, the batches were separated in an agarose gel, and the AKAP18δ and RIIα amplificates were eluted from the gel using the Geneclean method.

The AKAP18δ cDNA was cloned into the plasmid nicked with the restriction enzymes EcoRI and BamHI, which encodes the cyan-fluorescent protein (CFP) (PECFP, BD Biosciences). The RIIα cDNA was cloned into the plasmid nicked with the restriction enzymes EcoRI and BamHI, which encodes the yellow-fluorescent protein (YFP) (pEYFP, BD Biosciences). Consequently, the resulting plasmids encode the fusion proteins AKAP18δ-CFP and RIIα-YFP, respectively. *Escherichia coli* bacteria (strain JM109) were transformed with plasmid DNA. The plasmid DNA propagated in the bacteria was isolated using the Qiagen Midi-Plasmid preparation method according to the manufacturer's instructions (Qiagen, Hilden, Germany) and introduced in HEK293 cells by means of transfection (vide infra).

HEK293 cells (GBF, Brunswick) were cultured on polylysine-coated 30 mm cover glasses with 10% fetal calf serum (FCS) in Dulbecco's Minimal Eagle medium (DMEM) until a confluence of 40-60% was reached. The cells were transiently transfected with the AKAP18δ-CFP and RIIα-YFP plasmids (1-2 µg per DNA) (ratio of AKAP18δ-CFP/RIIα-YFP plasmid DNAs 1:4) using the Liptofectamine method (Gibco Invitrogen, Karlsruhe, Germany).

Fluorescence Resonance Energy Transfer (FRET) Measurements

HEK293 cells were transiently co-transfected with the plasmids encoding RIIα-YFP and AKAP18δ-CFP. FRET measurements were performed 24-48 hours after transfection, using an epifluorescence microscope (Axiovert 200M, Carl Zeiss, Jena, Germany). The data were stored using the Openlab 2.25 software (Improvision, Coventry GB). Fluorescence was excited at a wavelength of 425 nm for CFP and 488 nm for YFP. The emitted fluorescence was measured at a wavelength of 480/30 nm for CFP and 535/26 nm for YFP. The FRET of CFP to YFP was determined by excitation of CFP at a wavelength of 425 nm and measurement of the emission of YFP at a wavelength of 535/26 nm. Non-specific background fluorescence was determined in a region with no cells and subtracted. As the settings on the microscope remained unchanged, a 535/480 ratio >0.6 was taken as a positive FRET signal in all experiments.

In FRET experiments it is necessary to exclude false-positive signals resulting from co-excitation of YFP in addition to CFP. Furthermore, the radiation of CFP emission is also present in the YFP emission range. The control experiment for the detection of truly positive FRET signals involves an acceptor bleaching protocol (donor recovery after acceptor bleaching). The experiment was carried out on an inverse epifluorescence microscope (Axiovert 100, Carl Zeiss, Jena, Germany). In this experiment, the emission at 480/30 and 535/26 nm at an excitation of 425 nm is recorded using a 12 bit CCD camera (Imago, TILL-Photonics, Martinsried, Germany). Determination of the base signals is followed by strong excitation of YFP at a wavelength of 488 nm, resulting in loss of the YFP emission signals (acceptor bleaching). The emission of CFP determined at a wavelength of 480/30 nm immediately rises as FRET is interrupted (donor recovery). In this system YFP required repeated strong excitation at a wavelength of 488 nm because the energy of the light source was insufficient. Thus, bleaching and concomitant loss of the YFP emission signals takes place in steps. As a result, the emission of CFP determined at a wavelength of 480/30 nm rises continuously, rather than in a single step. The increase of CFP emission is therefore measured over a time period of approximately 120 s after the onset of acceptor bleaching.

To further investigate the specificity of the FRET, and to test the suitability of the co-transfected HEK293 cells for the identification of membrane-permeable substances modulating the interaction between RIIα-YFP and AKAP18δ-CFP, the cells were incubated with the membrane-permeable peptide S-Ht31 (100 µM) which inhibits AKAP-RII interactions in general. For control, the cells were incubated with the peptide S-Ht31-P which has no influence on the AKAP-RII interaction (Klußmann et al., J. Biol. Chem. 274, 4934-4938, 1999). FRET measurements were performed at intervals of 10 min for a total of 90 min.

Result

For direct detection of an interaction of AKAP18δ and regulatory RIIα subunits of PKA in vivo, HEK293 was co-transfected with plasmids encoding AKAP18δ-CFP and RIIα-YFP. FIG. 2 demonstrates co-expression of both proteins in the same cells. Expression of RIIα-YFP was detected by excitation at 488 nm and measurement of the emitted fluorescence at 535/26 nm (FIG. 2A), and that of AKAP18δ-CFP by excitation of fluorescence at 425 nm and measurement of the emitted fluorescence at 480/30 nm (FIG. 2B). Both fusion proteins exhibited diffuse, cytosolic distribution. Subsequently, the same cells were subjected to FRET measurements. To this end, the CFP donor is excited at a wavelength of 425 nm. If a suitable acceptor is in close vicinity (distance <10 nm), excitation of the donor results in partial energy transfer to the acceptor YFP which then fluoresces at a wavelength of 545 nm (schematic diagram in FIG. 3). Thus, to detect a FRET, the HEK293 cells (CFP) were excited at a wavelength of 425 nm, and the emission of YFP was measured at a wavelength of 535/26 nm. FIG. 2C shows a similar distribution of the illustrated YFP emission as in FIG. 2A. Consequently, an energy transfer from CFP to YFP has occurred. FIG. 1D shows a color-coded illustration of the calculated 535/480 ratio of approximately 1.2-1.5 of FRET signals in these cells.

Figure 4B:
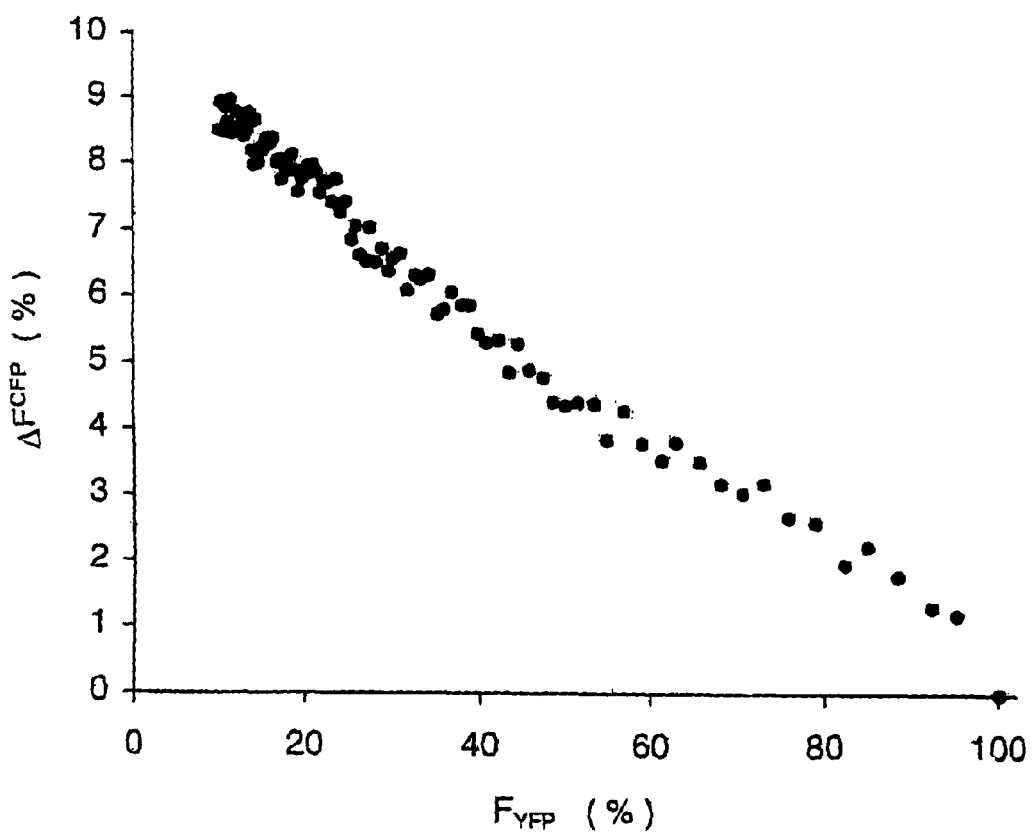
FIG. 4B shows a regression analysis of $\Delta F^{CFP}$ (%) vs. $\Delta F^{YFP}$(%).

The specificity of the measured FRET signals was examined using the acceptor bleaching protocol. FIG. 4A describes the kinetics of the fluorescence emitted by YFP and CFP, illustrating the ratio $F/F_{max}$ as a function of time (time in s). $F_{max}$ corresponds to maximum emission of YFP and CFP, respectively. Prior to acceptor bleaching, $F/F_{max}$ of YFP is approximately-1, and that of CFP approximately 0.92. Acceptor bleaching, beginning after 40 s, leads to a massive decrease of the emission signal of YFP. The $F/F_{max}$ of CFP rises from about 0.91 to about 1. The CFP emission increase of about 10% gives a FRET efficiency of about 10%. This observation is confirmed by regression analysis (FIG. 4B). The data show direct interaction of AKAP18δ and RIIα.

To further investigate the specificity of the interaction of AKAP18δ and RIIα and thus, that of the FRET, but also, to test the suitability of the co-transfected HEK293 cells for the identification of membrane-permeable substances modulating the interaction between AKAP18δ and RIIα, FRET measurements were carried out in the presence of the membrane-permeable peptide S-Ht31. This peptide inhibits the interaction between AKAP and regulatory PKA subunits in general (Klussmann et al., J. Biol. Chem. 274, 4934-4938, 1999; see schematic diagram in FIGS. 5A and B). FIG. 6A shows the color-coded FRET signal (535/480 ratio) from AKAP18δ to RIIα in two HEK293 cells. Prior to addition of S-Ht31 (time 0 min), the 535/480 ratio was about 1.3. A decrease of the 535/480 ratio (less red) directly correlates with the decrease of the interaction of CFP and YFP. Addition of S-Ht31 (100 μM, after time 0) induced a decrease of the 535/480 nm ratio by more than 50% within 80 min. The mean value of the ratio was about 0.35. FIG. 6B shows cells incubated with ineffective control peptide S-Ht31-P which has no influence on the AKAP-RII interaction. In this case, the color-coded FRET signal barely undergoes any change. FIG. 6C shows the summarized data obtained from FIGS. 6A and B, illustrating the change of the FRET signal (in %) as a function of time. The graphic diagram shows the FRET signal change observed on the cells in the presence of S-Ht31 or S-Ht31-P.

These results show that HEK293 cells co-expressing AKAP188-CFP and RIIα-YFP represent a suitable system for the identification of membrane-permeable substances inhibiting the interaction between such AKAP and RIIα.

AKAP binds regulatory PKA subunits via a conserved structural motif (amphipathic helix). Therefore, interaction of any AKAP with a regulatory PKA subunit can be detected in this system by means of FRET. This potential implies that the system can be utilized in a search for specific, membrane-permeable inhibitors for any AKAP-PKA interaction.

Figure 7:
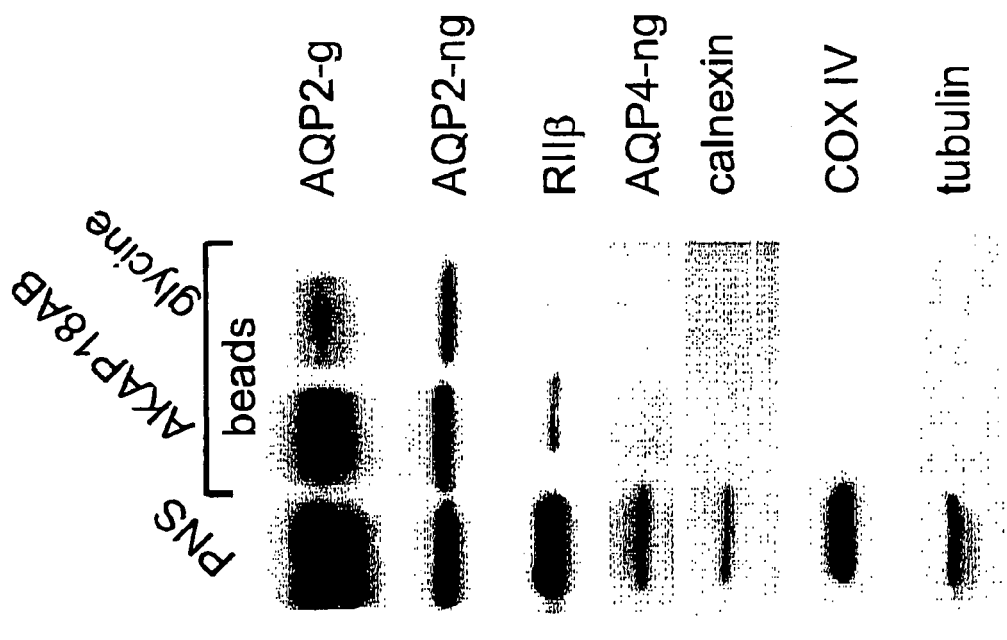
FIG. 7 shows that AQP2, PKA and AKAP18δ and/or a 55 kDa AKAP are present on the same intracellular vesicles.

AKAP18δ and AKAP18γ have different primary structures, which is why their subcellular and tissue-specific distribution is different, and this is also responsible for their different functions. Thus, for example, AKAP18γ is present in the nucleus of mouse oocytes, possibly playing a role in gene transcription (Brown et al., 2003). Moreover, AKAP18γ has been found in cytosolic and particulate fractions of rat kidney cells not identified in detail. Identification of the cell type(s) was not possible during these experiments because homogenates of whole kidneys had been used. Following ultracentrifugation of the homogenates, supernatants' and sediments were referred to as cytosolic or particulate fractions, e.g. by Trotter et al. (1999). The present inventors have demonstrated that AKAP18γ occurs both in the cytosol and in the nucleus of chief cells of the renal collecting tubules of rats. In such chief cells, the antidiuretic hormone arginine-vasopressin (AVP) regulates the water reabsorption by redistributing the water channel aquaporin-2 (AQP2) from intracellular vesicles to the urine side of the plasma membrane (Klussmann et al., 2000). The function of AKAP18γ in the chief cells is unknown. Like AKAP18γ, AKAP18δ is located in the cytosol and in the nucleus of renal chief cells, but in contrast to AKAP18γ, it is co-localized with AQP2 on intracellular vesicles (FIG. 7). The vesicles also contain regulatory RIIβ-PKA subunits, but lack proteins typically or exclusively occurring on other cell organelles (FIG. 7). AKAP18δ is therefore capable of anchoring PKA on the vesicles, which function cannot be assumed by the well-known AKAP18γ. Furthermore, it has been possible to demonstrate direct involvement of the inventive AKAP18δ in vasopressin-mediated water reabsorption in renal chief cells, using FRET experiments, for example, to which end CD8 cells have been used as model system (Valenti et al., 1996), the latter being a permanent cell line from rabbit kidneys, which stably express rat AQP2. In analogy to stimulation of native chief cells by vasopressin, stimulation of the cells with forskolin (direct activator of adenylyl cyclase, skipping of vasopressin receptor activation) results in translocation of AQP2 into the apical plasma membrane. As set forth in detail below, the CD8 cells were co-transfected with the AKAP18δ-CFP and RIIα-YFP constructs according to the invention. Stimulation of the cells with forskolin not only induced translocation of AQP2 into the apical plasma membrane, but also dissociation of AKAP and PKA (FIG. 8). The molecular mechanism of dissociation is possibly based on phosphorylation of a PKA consensus phosphorylation sequence at the PKA binding site of the AKAP. Such phosphorylation prevents binding of PKA to AKAP18δ as a result of electrostatic repulsion.

In addition to the general differences in structure and function between the well-known and new splicing variants, it has also been possible to demonstrate significant organ-specific differences. In contrast to the well-known splicing variant, AKAP18δ anchors PKA on $Ca^{2+}$ channels and receptors in myocardial cells.

Figure 9:
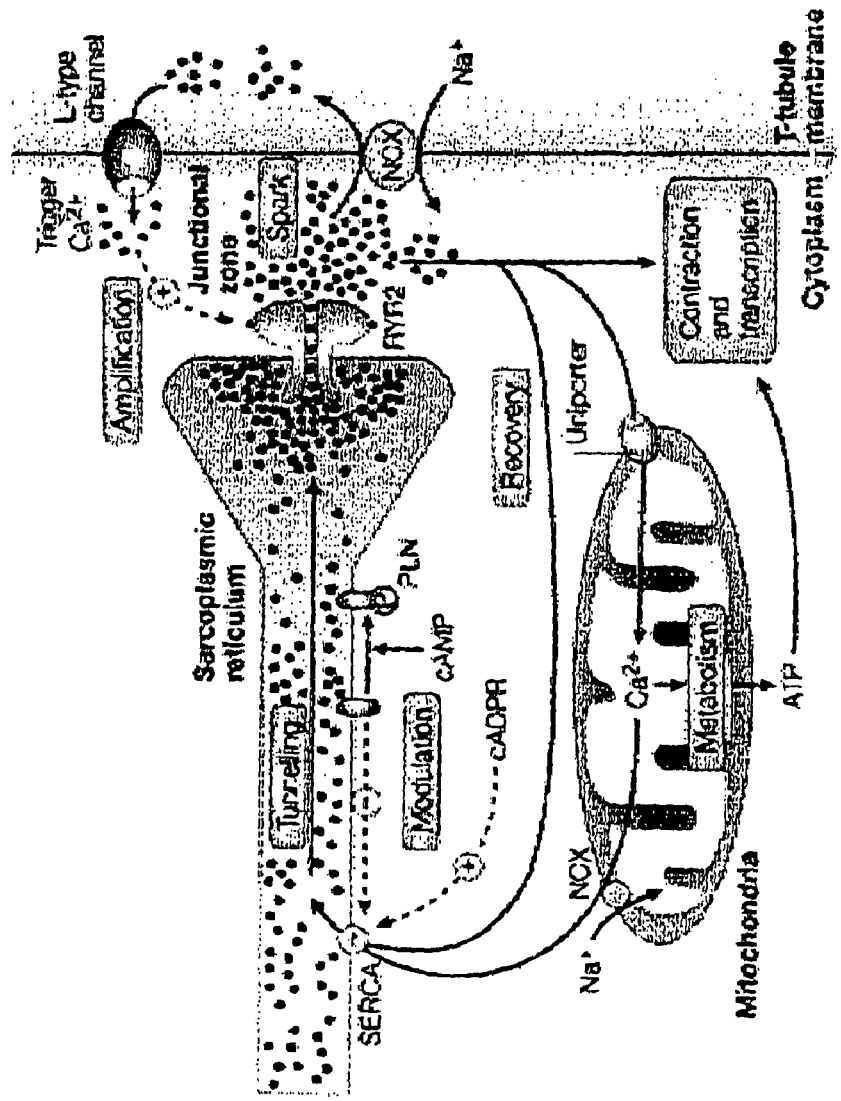
FIG. 9 is an illustration from Berridge et al. "Calcium signaling: Dynamics, homeostasis and remodelling." *Nature Rev. Mol Cell. Biol.*, 4, 517-529, 2003. The illustration outlines the role of $Ca^{2+}$ in intracellular signaling and in the remodeling of myocardial cells.

Myocardial contraction is caused by an increase of cytosolic $Ca^{2+}$ in myocardial cells (Berridge et al., 2003; FIG. 9). $Ca^{2+}$ enters the cells from the outside through L-type $Ca^{2+}$ channels after an action potential has reached the cells and caused opening of the channels located in the plasma membrane. The infiltrating $Ca^{2+}$ binds to ryanodin R2 receptors (RyR2) of the sarcoplasmic reticulum (SR), activates them, and induces efflux of $Ca^{2+}$ out of the SR through RyR2 and into the cytosol. Via several intermediate steps, the cytosolic $Ca^{2+}$ causes contraction of the cytoskeleton and thus of the myocardial cell. By back-pumping the $Ca^{2+}$ out of the cytosol and into the SR, the $Ca^{2+}$-ATPase SERCA2a is substantially involved in the termination of contraction. SERCA2a is inhibited by binding of the protein phospholamban (PLN). With increasing cytosolic $Ca^{2+}$, the inhibition is terminated by dissociation of the PLN from SERCA2a.

The intensity of myocardial cell contraction and thus, the intensity of contraction of the entire heart muscle, is modulated by the amount of $Ca^{2+}$ in the cytosol. One physiological modulator of the amount of $Ca^{2+}$ in myocardial cells is e.g. adrenaline which binds to the β-receptors on the surface of myocardial cells. Binding to these receptors is followed by activation of PKA, thereby phosphorylating the L-type $Ca^{2+}$ channels, RyR2, PLN, and the cytoskeletal protein troponin C. Phosphorylation of L-type $Ca^{2+}$ channels and RyR2 enhances the $Ca^{2+}$ conductivity thereof, thus increasing the cytosolic $Ca^{2+}$ concentration. Phosphorylated troponin C increases the contractility of the cytoskeleton. Phosphorylation of PLB causes dissociation thereof from SERCA2a and thus enhanced back-transport of $Ca^{2+}$ from the cytosol and into the SR. As a result, more $Ca^{2+}$ for influx into the cytosol is available for the next myocardial contraction. So-called β-blockers which, for example, are used in the therapy of hypertension prevent such phosphorylation incidents by blocking the β-receptors, thereby lowering the cardiac contractility and heart rate.

Thus, in Western blot investigations according to the invention it was demonstrated that AKAP18δ is expressed in the heart, whereas AKAP18γ is not. Investigations with an anti-AKAP18δ antibody using immunofluorescence microscopy (FIG. 10) show co-localization of AKAP18δ with RyR2, SERCA2a and PLN. Further, AKAP18δ co-localizes with the regulatory RIIα and β-subunits of PKA in heart cells. Accordingly, it has been shown that AKAP18δ anchors PKA in spatial proximity to RyR2, SERCA2a and PLN, enabling phosphorylation thereof. AKAP18α, also referred to as AKAP15, is another splicing variant of the AKAP18 gene. The corresponding protein is constituted of 81 amino acids. It enables phosphorylation of L-type $Ca^{2+}$ channels in the skeletal muscle of rabbits by anchoring the PKA on the L-type $Ca^{2+}$ channel (Hulme et al., 2002).

As can be concluded from the above, AKAP18γ and AKAP18δ exhibit significant differences in their primary structure, their subcellular localization, tissue-specific distribution, and in their function.

FIG. 7. AQP2, PKA and AKAP18β and/or a 55 kDa AKAP are present on the same intracellular vesicles. The inner medulla of rat kidneys was homogenized, and the nuclei and cell debris were removed by centrifugation. The resulting post-nuclear supernatant was incubated with affinity-purified anti-AKAP18δ antibodies coupled to an Eupergit C1Z methacrylate matrix (AKAP18AB beads). Non-saturated binding sites were blocked by incubation with glycine. For control purposes, beads were coated with glycine only (glycine beads). Our biochemical analyses showed that the anti-AKAP18δ antibody in the particulate fraction of chief cells recognizes AKAP18δ and a 55 kDa AKAP. The antibody detected AKAP18γ in the soluble fraction of chief cells and in the nucleus thereof. Glycosylated (g) and non-glycosylated (ng) AQP2, regulatory RIIβ PKA subunits and—as control—markers for the plasma membrane (non-glycosylated AQP4, AQP4-ng), the endoplasmic reticulum (calnexin), mitochondria (cytochrome C oxidase subunit IV, COX IV) and the cytoskeleton (tubulin) were detected by means of Western blot using commercially available antibodies.

FIG. 8. AKAP18δ plays a role in the signal cascade resulting in translocation of AQP2 into the apical plasma membrane of renal chief cells. A: CD8 cells were cotransfected with plasmids encoding RIIα-YFP and AKAP18δ-CFP. The FRET was measured prior to and after stimulation of the cells with forskolin (100 μM). Illustrated are two representative cells, each one co-expressing two fusion proteins. The FRET was measured prior to forskolin administration (0 s) and 95 and 600 s later on (95 s and 600 s). The FRET signal (535/480 nm ratio) is coded in pseudo-colors. B: Quantitative analysis of the effect of forskolin on the FRET signal (n=6 cells). Scale 20 μm.

FIG. 9. Calcium signals in the heart (taken from Berridge et al., 2003). Local $Ca^{2+}$ signals are responsible for the contraction and possibly for gene transcription ($Ca^{2+}$, red circles). $Ca^{2+}$ signals ($Ca^{2+}$ signalling) start with their amplification near L-type $Ca^{2+}$ channels on the T-tubules. Referred to as T-tubules are regions in the heart where the plasma membrane of heart cells and the membrane of the sarcoplasmic reticulum (SR) are in close proximity. Depolarization of the plasma membrane (T-tubule membrane) leads to a local, pulsed increase of cytosolic $Ca^{2+}$ which then diffuses to the ryanodin R2 receptor 2 (RyR2) and activates RyR2. Thereafter, $Ca^{2+}$ moves out of the SR, enters the cytosol (cytoplasm) through RyR2, diffusing from there until causing contraction. Contraction is terminated in that $Ca^{2+}$ is pumped out of the cells through the $Na^+/Ca^{2+}$ exchanger (NCX) or is pumped back through SERCA and into the SR. Part of the $Ca^{2+}$ migrates across the mitochondria where it stimulates metabolic processes providing ATP for contraction and transcription. In the SR, $Ca^{2+}$ specifically reaches the SR membrane located on the T-tubules (tunnelling), being liberated for the next heartbeat. The circulation of $Ca^{2+}$ is modulated by second messengers such as cyclic AMP (cAMP). Cyclic AMP stops the inhibitory effect of phospholamban (PLN). Another second messenger, cyclic ADP-ribose (cADPR), activates SERCA, so that a major amount of releasable $Ca^{2+}$ is present in the SR.

Figure 10:
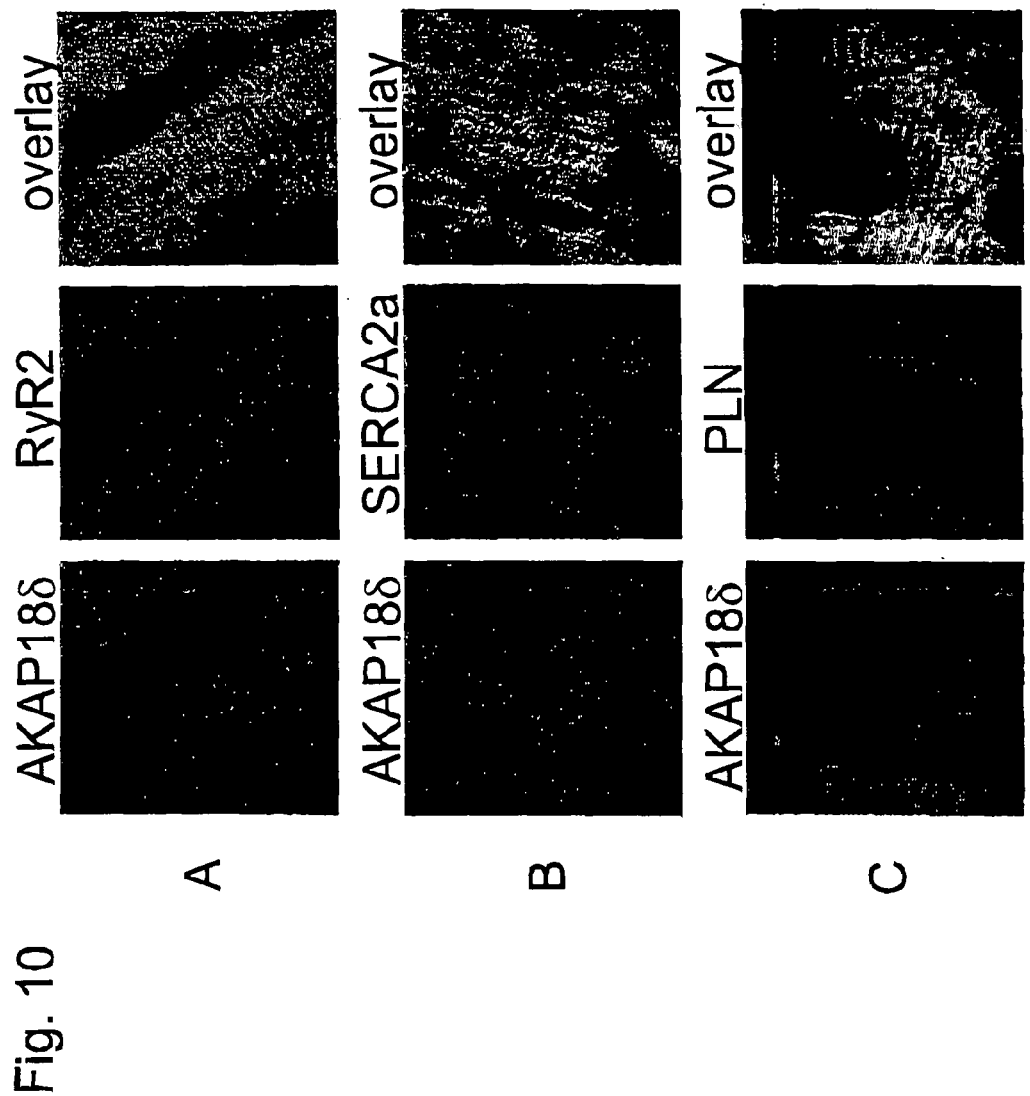
FIG. 10 shows co-localization of AKAP18δ with ryanodin R2 receptor 2 (RyR2), SERCA2a, phospholamban (PLN), regulatory RIIα and RIIβ subunits of PKA in rat heart cells, as detected via immunofluorescence microscopy.
Figure 10:
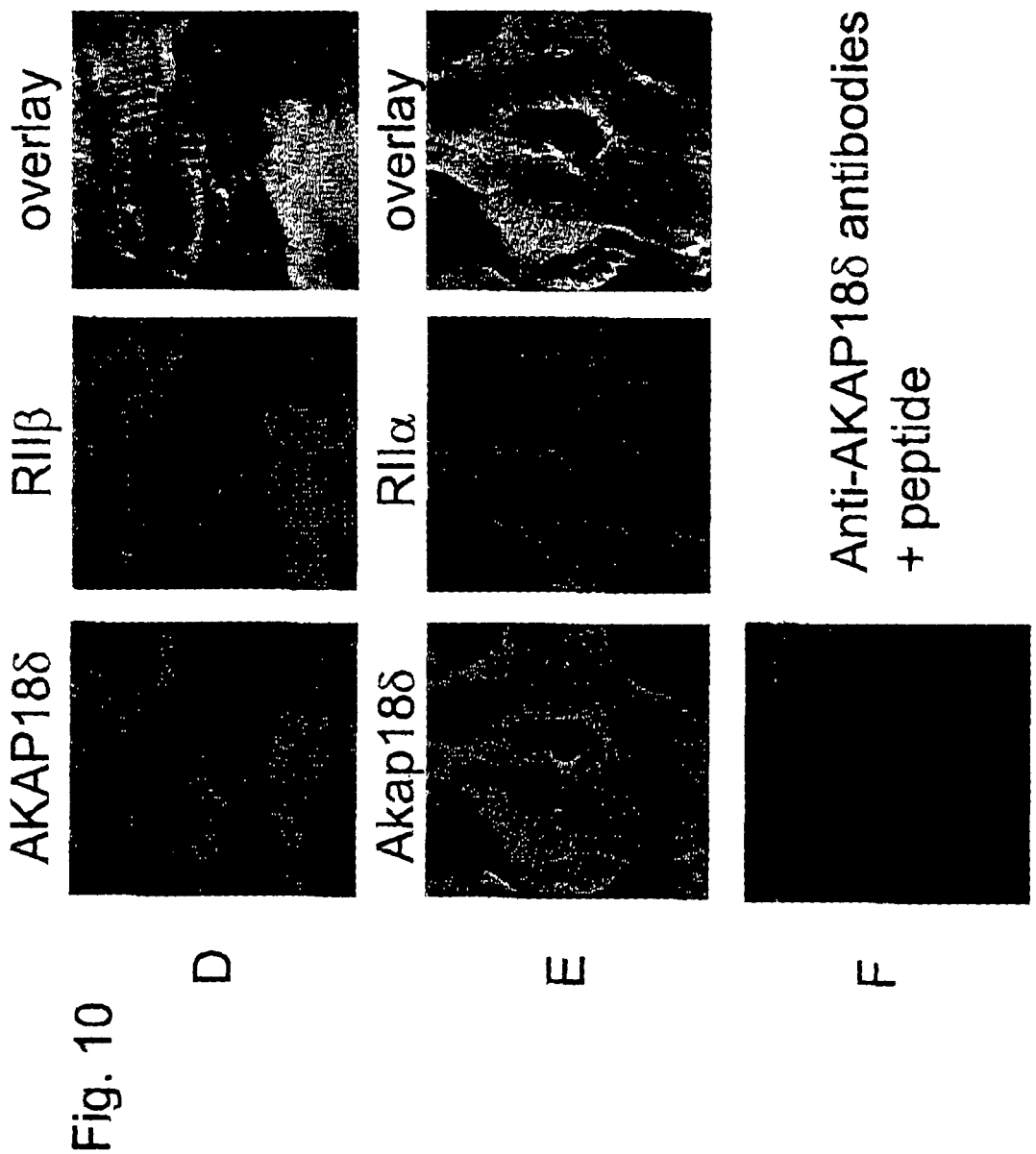

FIG. 10. Localization of AKAP18δ, ryanodin R2 receptor 2 (RyR2), SERCA2a and phospholamban (PLN), regulatory RIIα and β subunits of PKA in rat heart cells. Rat hearts were used to produce 5 μm sections. AKAP18δ was detected by means of an anti-AKAP18δ antibody produced and characterized by us (Henn et al., manuscript in preparation) and Cy3-coupled secondary antibodies. Simultaneous detection of the proteins specified in the Figure was effected using commercially available antibodies and Cy5-coupled secondary antibodies. The Cy3 and Cy5 fluorescence signals (green and red, respectively) were recorded with a laser scanning microscope (LSM 510, Zeiss, Jena, Germany). Co-localization of AKAP18δ with other proteins becomes apparent in the overlay by a yellow coloration.

LITERATURE

Berridge, M. J., Bootman, M. D., and Roderick, H. L. (2003), Calcium signalling: Dynamics, homeostasis and remodelling. Nature Rev. Mol Cell. Biol., 4, 517-529.

Brown, R. L., August, S. L, Williams, C. J. and Moss, S. B. (2003), AKAP7γ is a nuclear RI-binding AKAP. Biochem. Biophys. Res. Comm., 306, 394-401.

Henn, V. Edemir, B., Stefan, E., Schmitt, R., Vossebein, L., Lorenz, D., Tamma, G., Beyermann, M., Krause, E., Herberg, F. W., Valenti, G., Bachmann, S., Rosenthal, W., and Klussmann, E., Evidence for a role of novel A-kinase anchoring protein 18 isoforms in the vasopressin-induced aquaporin-2 shuttle in renal principal cells. Manuscript in preparation.

Hulme, J. T., Ahn, M., Hauschka, S. D., Scheuer, T. and Catterall, W. A. (2002), A novel leucine zipper targets AKAP15 and cyclic AMP-dependent protein kinase to the C terminus of the skeletal muscle $Ca^{2+}$ channel and modulates its function. J. Biol. Chem., 277, 4079-4087.

Klussmann, E., Maric, K. and Rosenthal, W. (2000), The mechanisms of aquaporin control in the renal collecting duct. Rev. Physiol. Biochem. Pharmacol., 141, 33-95.

Trotter, K. W., Fraser, I. D., Scott, G. K., Stutts, M. J., Scott, J. D. and Milgram, S. L. (1999), Alternative splicing regulates the subcellular localization of A-kinase anchoring protein 18 isoforms. J. Cell Biol., 147, 1481-1492.

Valenti, G., Frigeri, A., Ronco, P. M., D'Ettorre, C. and Svelto, M. (1996), Expression and functional analysis of water channels in a stably AQP2-transfected human collecting duct cell line. J. Biol. Chem., 271, 24365-24370; correction (1997) J. Biol. Chem. 272, 26794.

We claim:

1. An isolated nucleic acid molecule which is:
   (a) a nucleic acid molecule comprising the polynucleotide sequence of SEQ ID NO: 1;
   (b) a nucleic acid molecule which encodes a polypeptide comprising the sequence of SEQ ID NO: 2;
   (c) a nucleic acid molecule which consists of the polynucleotide sequence of SEQ ID NO: 1;
   (d) a nucleic acid molecule which encodes the polypeptide sequence of SEQ ID NO: 2; or
   (e) the complimentary nucleic acid sequence to the nucleic acid molecule of (c).

2. The isolated nucleic acid molecule according to claim 1(a), which encodes a polypeptide comprising the sequence set forth in SEQ ID NO: 2.

3. The isolated nucleic acid molecule according to claim 1, which is a genomic DNA, a cDNA or an RNA.

4. A vector comprising at least one isolated nucleic acid molecule according to claim 1.

5. A host cell comprising the vector according to claim 4.

6. A pharmaceutical composition comprising the isolated nucleic acid molecule according to claim 1 and a pharmaceutically tolerable carrier.

7. A kit which comprises the isolated nucleic acid molecule according claim 1 and a pharmaceutically tolerable carrier.

8. An isolated nucleic acid molecule which consists of the polynucleotide sequence set forth in SEQ ID NO: 1.

* * * * *

SEQUENCE LISTING

<160> NUMBER OF SEQ ID NOS: 6

<210> SEQ ID NO 1
<211> LENGTH: 1062
<212> TYPE: DNA
<213> ORGANISM: Rattus norvegicus

<400> SEQUENCE: 1

```
atggagcgcc ccgccgcggg agaaatagat gccaataagt gtgatcattt atcaagagga      60
gaggaaggga cggggacct ggagaccagc cctgtaggtt ctctggcaga cctgccgttt     120
gctgccgtag acattcaaga tgactgtgga ctccctgatg tacctcaagg aaatgtacct     180
caaggaaacc caaagagaag caagaaaat agaggcgaca ggaatgatca cgtgaagaag     240
aggaagaagg ccaagaaaga ttatcaaccc aactatttcc tgtccattcc aatcaccaac     300
aaaaagatta cagctggaat taaagtcttg caaaattcga tactgagaca ggataatcga     360
ttgaccaaag ccatggtcgg cgacggctcc tttcacatca ccttgctagt gatgcagcta     420
ttaaacgaag atgaagtaaa cataggtacc gacgcgcttt tggaactgaa gccgttcgtt     480
gaggagatcc ttgaggggaa gcatctgact ttgcccttcc acgggattgg cactttccaa     540
ggtcaggttg gctttgtgaa gctggcagac ggagatcacg tcagtgccct cctgggagata    600
gcagagactg caaaaaggac atttcaggaa aaaggcatcc tggctggaga agcagaact     660
tttaagcctc acctgacctt tatgaagctg tccaaagcac caatgctctg gaagaaggga    720
gtgagaaaaa tagagcctgg attgtatgag caatttatcg accacagatt tggagaagaa    780
atactgtacc aaatagatct ctgctccatg ctgaagaaaa aacagagcaa tggttattac    840
cactgcgagt cttcgatcgt gatcggtgag aaggaccgaa aggagcctga ggatgctgaa    900
ctggtcaggc tcagtaagag gctggtggag aacgccgtgc tcaaggctgt ccagcagtac    960
ctagaagaga cacagaacaa aaagcagccg ggggagggga actccgtcaa agctgaggag   1020
ggagatcgga atggcgatgg cagtgataac aaccggaagt ga                       1062
```

<210> SEQ ID NO 2
<211> LENGTH: 353
<212> TYPE: PRT
<213> ORGANISM: Rattus norvegicus

<400> SEQUENCE: 2

```
Met Glu Arg Pro Ala Ala Gly Glu Ile Asp Ala Asn Lys Cys Asp His
 1               5                  10                  15

Leu Ser Arg Gly Glu Glu Gly Thr Gly Asp Leu Glu Thr Ser Pro Val
            20                  25                  30

Gly Ser Leu Ala Asp Leu Pro Phe Ala Ala Val Asp Ile Gln Asp Asp
        35                  40                  45

Cys Gly Leu Pro Asp Val Pro Gln Gly Asn Val Pro Gln Gly Asn Pro
    50                  55                  60

Lys Arg Ser Lys Glu Asn Arg Gly Asp Arg Asn Asp His Val Lys Lys
65                  70                  75                  80

Arg Lys Lys Ala Lys Lys Asp Tyr Gln Pro Asn Tyr Phe Leu Ser Ile
                85                  90                  95

Pro Ile Thr Asn Lys Lys Ile Thr Ala Gly Ile Lys Val Leu Gln Asn
            100                 105                 110

Ser Ile Leu Arg Gln Asp Asn Arg Leu Thr Lys Ala Met Val Gly Asp
        115                 120                 125
```

```
Gly Ser Phe His Ile Thr Leu Leu Val Met Gln Leu Leu Asn Glu Asp
        130                 135                 140

Glu Val Asn Ile Gly Thr Asp Ala Leu Leu Glu Leu Lys Pro Phe Val
145                 150                 155                 160

Glu Glu Ile Leu Glu Gly Lys His Leu Thr Leu Pro Phe His Gly Ile
                165                 170                 175

Gly Thr Phe Gln Gly Gln Val Gly Phe Val Lys Leu Ala Asp Gly Asp
            180                 185                 190

His Val Ser Ala Leu Leu Glu Ile Ala Glu Thr Ala Lys Arg Thr Phe
        195                 200                 205

Gln Glu Lys Gly Ile Leu Ala Gly Glu Ser Arg Thr Phe Lys Pro His
    210                 215                 220

Leu Thr Phe Met Lys Leu Ser Lys Ala Pro Met Leu Trp Lys Lys Gly
225                 230                 235                 240

Val Arg Lys Ile Glu Pro Gly Leu Tyr Glu Gln Phe Ile Asp His Arg
                245                 250                 255

Phe Gly Glu Glu Ile Leu Tyr Gln Ile Asp Leu Cys Ser Met Leu Lys
            260                 265                 270

Lys Lys Gln Ser Asn Gly Tyr Tyr His Cys Glu Ser Ser Ile Val Ile
        275                 280                 285

Gly Glu Lys Asp Arg Lys Glu Pro Glu Asp Ala Glu Leu Val Arg Leu
    290                 295                 300

Ser Lys Arg Leu Val Glu Asn Ala Val Leu Lys Ala Val Gln Gln Tyr
305                 310                 315                 320

Leu Glu Glu Thr Gln Asn Lys Lys Gln Pro Gly Glu Gly Asn Ser Val
                325                 330                 335

Lys Ala Glu Glu Gly Asp Arg Asn Gly Asp Gly Ser Asp Asn Asn Arg
            340                 345                 350

Lys

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcgagctca agcttcgaat tctgatggag cgccccgccg cggg            44

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcgaccggt ggatcccggg cccggttgtt atcactgcca tcgcc           45

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
tcagatctcg agctcaagct tcgaattctg atgagccaca tccagatccc g          51

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaccggtgga tcccgggcct gcccgaggtt gcccagat                          38
```